US012655198B2

(12) United States Patent
Thompson et al.

(10) Patent No.: US 12,655,198 B2
(45) Date of Patent: Jun. 16, 2026

(54) RAPID AND SIMPLE PURIFICATION OF ELASTIN-LIKE POLYPEPTIDES DIRECTLY FROM WHOLE CELLS AND CELL LYSATES BY ORGANIC SOLVENT EXTRACTION

(71) Applicant: Purdue Research Foundation, West Lafayette, IN (US)

(72) Inventors: David Harley Thompson, West Lafayette, IN (US); Craig Sweet, West Lafayette, IN (US); Aayush Aayush, West Lafayette, IN (US); Ross VerHeul, West Lafayette, IN (US)

(73) Assignee: Pudue Research Foundation, West Lafayette, IN (US)

( * ) Notice: Subject to any disclaimer, the term of this patent is extended or adjusted under 35 U.S.C. 154(b) by 451 days.

(21) Appl. No.: 16/975,431

(22) PCT Filed: Feb. 25, 2019

(86) PCT No.: PCT/US2019/019468
§ 371 (c)(1),
(2) Date: Aug. 25, 2020

(87) PCT Pub. No.: WO2019/165390
PCT Pub. Date: Aug. 29, 2019

(65) Prior Publication Data
US 2021/0054048 A1    Feb. 25, 2021

Related U.S. Application Data

(60) Provisional application No. 62/635,309, filed on Feb. 26, 2018.

(51) Int. Cl.
*C07K 14/78*      (2006.01)
*C07K 1/13*      (2006.01)

(52) U.S. Cl.
CPC ............... *C07K 14/78* (2013.01); *C07K 1/13* (2013.01)

(58) Field of Classification Search
CPC ........... C07K 14/78; C07K 1/13; C12N 15/09
See application file for complete search history.

(56) References Cited

U.S. PATENT DOCUMENTS

| | | | |
|---|---|---|---|
| 9,102,763 B2 | 8/2015 | MacKay et al. | |
| 2008/0188642 A1* | 8/2008 | Ying | C07K 14/78 530/425 |
| 2012/0045805 A1* | 2/2012 | Sadeghi Pour Marvi | C12P 7/625 435/146 |
| 2017/0082606 A1* | 3/2017 | Caprioli | G01N 33/573 |

FOREIGN PATENT DOCUMENTS

| JP | H0564591 A | * | 3/1993 |
|---|---|---|---|
| WO | WO-2013016566 A1 | * | 1/2013 |

OTHER PUBLICATIONS

Chacon-Cortes D, Griffiths L. Methods for extracting genomic DNA from whole blood samples: current perspectives. Journal of Biorepository Science for Applied Medicine. 2014;2:1-9 https://doi.org/10.2147/BSAM.S46573 (Year: 2014).*
Sandberg LB, Wolt TB. Production and isolation of soluble elastin from copper-deficient swine. Methods Enzymol. 1982;82 Pt A:657-65. doi: 10.1016/0076-6879(82)82094-6. PMID: 7078451. (Year: 1982).*
Waghu FH, Barai RS, Gurung P, Idicula-Thomas S. CAMPR3: a database on sequences, structures and signatures of antimicrobial peptides. Nucleic Acids Res. Jan. 4, 2016;44(D1):D1094-7. doi: 10.1093/nar/gkv1051. Epub Oct. 13, 2015. PMID: 26467475; PMCID: PMC4702787. (Year: 2015).*
Sardessai YN, Bhosle S. Industrial potential of organic solvent tolerant bacteria. Biotechnol Prog. May-Jun. 2004;20(3):655-60. doi: 10.1021/bp0200595. PMID: 15176865. (Year: 2004).*
Martinez-Aragon et al (Separation and Purification Technology, vol. 65, Issue 1, Feb. 2009.*
MacEwan, S.R. et al., "Non-Chromatographic Purification of Recombinant Elastin-Like Polypeptides and their Fusions with Peptides and Proteins from *Escherichia coli*," Journal of Visualized Experiments, 88, Copyright 2014, pp. 1-8.
International Search Report and Written Opinion, dated Jul. 29, 2019, for International Application No. PCT/US19/19468, (7 pages).
Bahniuk, M.S. et al., "High-Yield Recombinant Expression and Purification of Marginally Soluble, Short Elastin-Like Polypeptides," BioTechniques 61, (2016), pp. 297-304.
Jain, S. et al., "Purification of Recombinant Green Fluorescent Protein by Three-Phase Partitioning," Chromatogr. A, 1035 (2004), pp. 83-86.
Meyer, D.E. et al., "Purification of Recombinant Proteins by Fusion with Thermally-Responsive Polypeptides," Nature Biotechnology, vol. 17, (1999), pp. 1112-1115.
VerHeul, R. et al., "Rapid and Simple Purificaion of Elastin-Like Polypeptides Directly from Whole Cells and Cell Lysates by Organic Solvent Extraction," Biomater Sci. 6, (4), (2018), pp. 863-876.
Yakhnin, A.V. et al., "Green Fluorescent Protein Purification by Organic Extaction," Protein Expression and Purification, 14, Article No. PT980981, (1998), pp. 382-386.
Bidwell, G.L., et al., "A Kidney-Selective Biopolymer for Targeted Drug Delivery," Am J. Physiol Renal Physiol, 312, (Oct. 26, 2016), (11 pages).
Chow, D.C., et al., "Ultra-High Expression of a Thermally Responsive Recombinant Fusion Protein in *E. coli*," Biotechnol Prog, 22(3), (2006), (20 pages).

(Continued)

*Primary Examiner* — Gary B Nickol

(74) *Attorney, Agent, or Firm* — Purdue Research Foundation

(57)        ABSTRACT

Disclosed herein is an optimized Elastin-like peptide purification scheme from whole cell lysate that is broadly applicable to neutral, acidic or basic ELP polypeptide. The method involves the use of one or more organic solvent to extract the ELP polypeptide from whole lysate followed by optional back extraction, precipitation, hot spins, and/or dialysis to purify the target ELP polypeptide.

10 Claims, 35 Drawing Sheets
Specification includes a Sequence Listing.

(56) References Cited

OTHER PUBLICATIONS

Christensen, T., et al., "Fusion Order Controls Expression Level and Activity of Elastin-Like Polypeptide Fusion Proteins," Protein Science, vol. 18, (2009), (11 pages).

Christensen, T., et al., "Predicting Transition Temperatures of Elastin-Like Polypeptide Fusion Proteins," Biomacromolecules, 14(5), (May 13, 2013), (13 pages).

Christensen, T., et al., "Purfication of Recombinant Proteins from *E. coli* at Low Expression Levels by Inverse Transition Cycling," Anal. Biochem., 360(1), (Jan. 1, 2007), (7 pages).

Fong, B.A., et al., "Purification of *Escherichia coli* RNA Polymerase Using a Self-Cleaving Elastin-Like Polypeptide Tag," Protein Science, vol. 19, (2010), (10 pages).

Hassouneh, W., et al., "Elastin-Like Polypeptides as a Purfication Tag for Recombinant Proteins," Curr Protoc Protein Sci. Chaper: Unit-6.11., (Aug. 2010), (20 pages).

Hassouneh, W., et al., "Fusions of Elastin-Like Polypeptides to Pharmaceutical Proteins," Methods Enzymol, 502, (2012), (24 pages).

Jordan, S.W., et al., "The Effect of a Recombinant Elastin-Mimetic Coating of an ePTFE Prosthesis on Acute Thrombogenicity in a Baboon Arteriovenous Shunt," Biomaterials, 28, (2007), (7 pages).

Kowalczyk, T., et al., "Elastin-Like Polypeptides as a Promising Family of Genetically-Engineered Protein Based Polymers," World J Microbiol Biotechnol, 30, (2014), (12 pages).

Lim, D.W., et al., "Improved Non-Chromatographic Purification of a Recombinant Protein by Cationic Elastin-Like Polypeptides," Biomacromolecules, 8(5), (May 2007), (18 pages).

Martin, S.L., et al., "Total Synthesis and Expression in *Escherichia coli* of a Gene Encoding Human Tropoelastin," Gene, 154, (1995), (8 pages).

Mecham, P., "Methods in Elastic Tissue Biology: Elastin Isolation and Purification," Methods, 45(1), (May 2008), (18 pages).

Prosser, I.W., et al., "Polyclonal Antibodies to Tropoelastin and the Specific Detection and Measurement of Tropoelastin in Vitro," Connective Tissue Research, vol. 25, (1991), (15 pages).

Samarkina, O.N., et al., "Universal and Rapid Method for Purification of GFP-Like Proteins by the Ethanol Extraction," Protein Expression and Purfication, 65, (2009), (7 pages).

Sandberg, L.B., et al., "[*37] Production and Isolation of Soluble Elastin From Copper-Deficient Swine," Methods in Enzymology, vol. 82, (1982), (9 pages).

Sarangthem, V., et al., "Construction and Application of Elastin Like Polypeptide Containing IL-4 Receptor Targeting Peptide," PLOS ONE, vol. 8, Issue 12, (Dec. 2013), (12 pages).

Trabbic-Carlson, K., et al., "Expression and Purification of Recombinant Proteins from *Escherichia coli*: Comparison of an Elastin-Like Polypeptide Fusion with an Oligohistidine Fusion," Protein Science, 13, (2004), (11 pages).

Urry, D.W, "Free Energy Transduction in Polypeptides and Proteins Based on Inverse Temperature Transitions," Prog. Biophys. Molec. Biol., vol. 57, (1992), (35 pages).

Urry, D.W., et al., "Phase-Structure Transitions of the Elastin Polypentapeptide-Water System Within the Framework of Composition-Temperature Studies," Biopolymers, vol. 24, (1985), (12 pages).

Urry, D.W., "Physical Chemistry of Biological Free Energy Transduction as Demonstrated by Elastic Protein-Based Polymers," J. Phys. Chem. B, 101, (1997), (22 pages).

Urry, D.W., et al., "Temperature of Polypeptide Inverse Temperature Transition Depends on Mean Residue Hydrophobicity," J. Am. Chem. Soc., 113, (1991), (3 pages).

Wang, W., et al., "Protein Polymer Nanoparticles Engineered as Chaperones Protect Against Apoptosis in Human Retinal Pigment Epithelial Cells," J Control Release, 191, (Oct. 10, 2014), (25 pages).

Wrenn, D., et al., "Identification of Multiple Tropoelastins Secreted by Bovine Cells," The Journal of Biological Chemistry, vol. 262, No. 5, Issue of Feb. 15, 1987, (6 pages).

Yeboah, A., et al., "Elastin-Like Polypeptides: A Strategic Fusion Partner for Biologics," Biotechnology and Bioengineering, vol. 113, No. 8, (Aug. 2016), (11 pages).

* cited by examiner

L   BA

1-Blank
2-A
3-AB
4-AC
5-AD
6-AE
7-AF
8-AG
9-Blank
10-Ladder

N8 VPGXG$_{40}$ X= V

MW=16.62kDa

PI= 5.52

1-Blank
2-Ladder(bluestain2)
3-Blank
4-B
5-BC
6-BD
7-BE
8-BF
9-BG
10-C

Solvent Key

A=Isopropanol      E=Methanol

B=Butanol            F=Acetone

C=Ethyl Acetate   G=Acetonitrile

D=Ethanol

1-Blank
2-Blank
3-Ladder(Bluestain2)
5-CD
5-CE
6-CF
7-CG
8-D
9-DE
10-DF kDa
~245
~180
~135
~100
~75
~63
~48
~35
~25
~20
~17
~11
~6
Tris-Glycine
4-20%

1-DG
2-E
3-Blank
4-Ladder(Bluestain2)
5-Blank
6-EF
7-EG
8-F
8-FG
10-G

1-G
2-A
3-AB
4-AC
5-AD
6-AE
7-AF
8-AG
9-B
10-BC

1-BD
2-Ladder(bluestain2)
3-BE
4-BF
5-BG
6-C
7-CD
8-CE
9-CF
10-CG

1-D
2-DE
3-Ladder(Bluestain2)
4-DF
5-DG
6-E
7-EF
8-EG
9-F
10-FG kDa
~244
~180
~135
~100
~75
~63
~48
~35
~25
~20
~17
~11
~5

Tris-Glycine
4~20%

A8 VPGXG$_{40}$ X= V/I/E [1:3:1]

MW= 17.19

PI= 3.36

Solvent Key

A=Isopropanol     E=Methanol

B=Butanol     F=Acetone

C=Ethyl Acetate     G=Acetonitrile

D=Ethanol

1-Ladder(Bluestain2)
2-Blank
3-A
4-AB
5-AC
6-AD
7-AE
8-AF
9-AG
10-Blank

1-Blank
2-Ladder(bluestain2)
3-Blank
4-B
5-BC
6-BD
7-BE
8-BF
9-BG
10-C

1-CD
2-Blank
3-Ladder(Bluestain2)
4-Blank
5-CE
6-CF
7-CG
8-D
9-DE
10-DF kDa
~245
~180
~135
~100
~75
~63
~48
~35
~25
~20
~17
~11
~9
Tris-Glycine
4~20%

A16 VPGXG$_{80}$ X= V/I/E [1:3:1]

MW= 34.15

PI= 3.13

Solvent Key

A=Isopropanol          E=Methanol

B=Butanol               F=Acetone

C=Ethyl Acetate        G=Acetonitrile

D=Ethanol

1-DG
2-E
3-Blank
4-Ladder(Bluestain2)
5-Blank
6-EF
7-EG
8-F
9-FG
10-G

1: Methanol
2: Ladder
3: Ethanol: Methanol
4: Ethanol: 3 Methanol
5: Ethanol: 4 Methanol
6: Acetonitrile
7: Methanol:Acetonitrile
8: --
9: --
10: --

1 – Blank
2 - Ladder
3 – ACN pellet in water
4 – ACN pellet in PBS
5 – C2 super(water)
6 – C2 super (PBS)
7 – HSP1 in water
8 – HSP1 in PBS
9 – HSP2 in water
10 – HSP2 in PBS 1- Ladder
2- ACN super (water)
3- ACN super (PBS)
4- ACN super (Urea)
5- ACN super (triton)
6- Blank
7- HSP2 (water)
8- HSP2 (PBS)
9- HSP2 (Urea)
10- HSP2 (Triton)

1- ACN ppt
2- C2 sup
3- HSS1
4- HSP1
5- HSS1
6- HSP1
7- CSP1
8- CSS1
9- blank
10- ladder 1- ACN ppt (RT)
2- Acetone ppt (RT)
3- BE-ACN ppt (RT)
4- BE-Acetone (RT)
5- ACN ppt (cold)
6- Acetone ppt (cold)
7- ACN C2 super (cold)
8- Acetone C2 super (cold)
9- BE-ACN C2 super (RT)
10- Ladder 1- Ladder
2- C2 Super (ACN)
3- HSP (ACN)
4- C2 Super (acetone)
5- HSP(acetone)
6- C2 Super (ACN)(cold)
7- HSP (ACN)(cold)
8- C2 Super (acetone)(cold)
9- HSP (acetone)(cold)
10- Blank 1- ladder
2- extraction- IPA-BuOH
3- extraction-1HS
4- Extraction+BE
5- Extraction+BE+1HS
6- Extr+CAN
7- Extr+CAN+1HS
8- Lysate
9- Lysate+1HS-CS
10- Lysate+3HS-CS 1- Lysate
2- Lysate-1HS
3- Lysate-3HS
4- extraction
5- extraction+1HS
6- extraction+BE
7- extraction+BE+1HS
8- Extraction+CAN
9- Extr+CAN+1HS
10-Ladder

Optimized Elastin-like Peptide Purification Scheme

SEQUENCE LISTING

<160> NUMBER OF SEQ ID NOS: 15

<210> SEQ ID NO 1
<211> LENGTH: 245
<212> TYPE: PRT
<213> ORGANISM: artificial
<220> FEATURE:
<223> OTHER INFORMATION: GFP (green fluorescent protein, UV variant with
      an N-terminal polyhistidine tag)

<400> SEQUENCE: 1

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
        35                  40                  45

Thr Gly Lys Leu Pro Val Pro Trp Pro Thr Leu Val Thr Thr Phe Ser
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Asn Tyr Lys Thr Arg Ala Glu Val Lys
                100                 105                 110

Phe Glu Gly Asp Thr Leu Val Asn Arg Ile Glu Leu Lys Gly Ile Asp
            115                 120                 125

Phe Lys Glu Asp Gly Asn Ile Leu Gly His Lys Leu Glu Tyr Asn Tyr
    130                 135                 140

Asn Ser His Asn Val Tyr Ile Thr Ala Asp Lys Gln Lys Asn Gly Ile
145                 150                 155                 160

Lys Ala Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Lys Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys His His His
225                 230                 235                 240

His His His His His
                245

-continued

```
<210> SEQ ID NO 2
<211> LENGTH: 721
<212> TYPE: PRT
<213> ORGANISM: artificial
<220> FEATURE:
<223> OTHER INFORMATION: TEL  (human tropoelastin, main chain)

<400> SEQUENCE: 2

Gly Gly Val Pro Gly Ala Val Pro Gly Gly Val Pro Gly Gly Val Phe
1               5                   10                  15

Phe Pro Gly Ala Gly Leu Gly Gly Leu Gly Val Gly Gly Leu Gly Pro
                20                  25                  30

Gly Val Lys Pro Ala Lys Pro Gly Val Gly Gly Leu Val Gly Pro Gly
            35                  40                  45

Leu Gly Ala Glu Gly Ser Ala Leu Pro Gly Ala Phe Pro Gly Gly Phe
        50                  55                  60

Phe Gly Ala Gly Gly Gly Ala Ala Gly Ala Ala Ala Ala Tyr Lys Ala
65                  70                  75                  80

Ala Ala Lys Ala Gly Ala Ala Gly Leu Gly Val Gly Gly Ile Gly Gly
                85                  90                  95

Val Gly Gly Leu Gly Val Ser Thr Gly Ala Val Val Pro Gln Leu Gly
                100                 105                 110

Ala Gly Val Gly Ala Gly Val Lys Pro Gly Lys Val Pro Gly Val Gly
            115                 120                 125

Leu Pro Gly Val Tyr Pro Gly Gly Val Leu Pro Gly Ala Gly Ala Arg
        130                 135                 140

Phe Pro Gly Ile Gly Val Leu Pro Gly Val Pro Thr Gly Ala Gly Val
145                 150                 155                 160

Lys Pro Lys Ala Gln Val Gly Ala Gly Ala Phe Ala Gly Ile Pro Gly
                165                 170                 175

Val Gly Pro Phe Gly Gly Gln Gln Pro Gly Leu Pro Leu Gly Tyr Pro
                180                 185                 190

Ile Lys Ala Pro Lys Leu Pro Ala Gly Tyr Gly Leu Pro Tyr Lys Thr
            195                 200                 205

Gly Lys Leu Pro Tyr Gly Phe Gly Pro Gly Gly Val Ala Gly Ser Ala
        210                 215                 220

Gly Lys Ala Gly Tyr Pro Thr Gly Thr Gly Val Gly Pro Gln Ala Ala
225                 230                 235                 240

Ala Ala Ala Ala Lys Ala Ala Ala Lys Leu Gly Ala Gly Gly Ala Gly
                245                 250                 255

Val Leu Pro Gly Val Gly Val Gly Gly Pro Gly Ile Pro Gly Ala Pro
                260                 265                 270

Gly Ala Ile Pro Gly Ile Gly Gly Ile Ala Gly Val Gly Ala Pro Asp
            275                 280                 285

Ala Ala Ala Ala Ala Ala Ala Ala Ala Lys Ala Ala Lys Phe Gly Ala
        290                 295                 300

Ala Gly Gly Leu Pro Gly Val Gly Val Pro Gly Val Gly Val Pro Gly
305                 310                 315                 320

Val Gly Val Pro Gly Val Gly Val Pro Gly Val Gly Val Pro Gly Val
                325                 330                 335

Gly Val Pro Gly Val Gly Val Pro Gly Val Gly Val Pro Gly Val Gly
            340                 345                 350

Val Pro Gly Val Gly Val Pro Gly Val Gly Val Pro Gly Ala Leu Ser
        355                 360                 365
```

-continued

```
Pro Ala Ala Thr Ala Lys Ala Ala Lys Ala Ala Lys Phe Gly Ala
    370             375             380

Arg Gly Ala Val Gly Ile Gly Gly Ile Pro Thr Phe Gly Leu Gly Pro
385             390             395             400

Gly Gly Phe Pro Gly Ile Gly Asp Ala Ala Ala Pro Ala Ala Ala
            405             410             415

Ala Ala Lys Ala Ala Lys Ile Gly Ala Gly Gly Val Gly Ala Leu Gly
            420             425             430

Gly Val Val Pro Gly Ala Pro Gly Ala Ile Pro Gly Leu Pro Gly Val
            435             440             445

Gly Gly Val Pro Gly Val Gly Ile Pro Ala Ala Ala Ala Ala Lys Ala
    450             455             460

Ala Ala Lys Ala Ala Gln Phe Gly Leu Gly Pro Gly Val Gly Val Ala
465             470             475             480

Pro Gly Val Gly Val Val Pro Gly Val Gly Val Val Pro Gly Val Gly
            485             490             495

Val Ala Pro Gly Ile Gly Leu Gly Pro Gly Gly Val Ile Gly Ala Gly
            500             505             510

Val Pro Ala Ala Ala Lys Ser Ala Ala Lys Ala Ala Ala Lys Ala Gln
    515             520             525

Phe Arg Ala Ala Ala Gly Leu Pro Ala Gly Val Pro Gly Leu Gly Val
    530             535             540

Gly Ala Gly Val Pro Gly Leu Gly Val Gly Ala Gly Val Pro Gly Leu
545             550             555             560

Gly Val Gly Ala Gly Val Pro Gly Pro Gly Ala Val Pro Gly Thr Leu
            565             570             575

Ala Ala Ala Lys Ala Ala Lys Phe Gly Pro Gly Gly Val Gly Ala Leu
            580             585             590

Gly Gly Val Gly Asp Leu Gly Gly Ala Gly Ile Pro Gly Gly Val Ala
    595             600             605

Gly Val Val Pro Ala Ala Ala Ala Ala Ala Lys Ala Ala Ala Lys Ala
    610             615             620

Ala Gln Phe Gly Leu Gly Gly Val Gly Gly Leu Gly Val Gly Gly Leu
625             630             635             640

Gly Ala Val Pro Gly Ala Val Gly Leu Gly Gly Val Ser Pro Ala Ala
            645             650             655

Ala Ala Lys Ala Ala Lys Phe Gly Ala Ala Gly Leu Gly Gly Val Leu
            660             665             670

Gly Ala Gly Gln Pro Phe Pro Ile Gly Gly Gly Ala Gly Gly Leu Gly
            675             680             685

Val Gly Gly Lys Pro Pro Lys Pro Phe Gly Gly Ala Leu Gly Ala Leu
    690             695             700

Gly Phe Pro Gly Gly Ala Cys Leu Gly Lys Ser Cys Gly Arg Lys Arg
705             710             715             720

Lys
```

```
<210> SEQ ID NO 3
<211> LENGTH: 61
<212> TYPE: PRT
<213> ORGANISM: artificial
<220> FEATURE:
<223> OTHER INFORMATION: V12 monoblock

<400> SEQUENCE: 3

Val Pro Gly Val Gly Val Pro Gly Val Gly Val Pro Gly Val Gly Val
```

-continued

```
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Tyr
    50                  55                  60

<210> SEQ ID NO 4
<211> LENGTH: 121
<212> TYPE: PRT
<213> ORGANISM: artificial
<220> FEATURE:
<223> OTHER INFORMATION: V24 monoblock

<400> SEQUENCE: 4

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Tyr
    115                 120

<210> SEQ ID NO 5
<211> LENGTH: 146
<212> TYPE: PRT
<213> ORGANISM: artificial
<220> FEATURE:
<223> OTHER INFORMATION: S12-K4-S12 multiblock

<400> SEQUENCE: 5

Gly His His His His His His Asn Gly Trp Gly Val Pro Gly Ser Gly
1               5                   10                  15

Val Pro Gly Ser Gly Val Pro Gly Ser Gly Val Pro Gly Ser Gly Val
            20                  25                  30

Pro Gly Ser Gly Val Pro Gly Ser Gly Val Pro Gly Ser Gly Val Pro
        35                  40                  45

Gly Ser Gly Val Pro Gly Ser Gly Val Pro Gly Ser Gly Val Pro Gly
    50                  55                  60

Ser Gly Val Pro Gly Ser Gly Gly Gly Lys Gly Gly Lys Gly Gly Lys
65                  70                  75                  80

Gly Gly Lys Gly Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125
```

-continued

```
Ser Gly Val Pro Gly Ser Gly Val Pro Gly Ser Gly Val Pro Gly Ser
    130                 135                 140

Gly Tyr
145

<210> SEQ ID NO 6
<211> LENGTH: 146
<212> TYPE: PRT
<213> ORGANISM: artificial
<220> FEATURE:
<223> OTHER INFORMATION: V12-K4-V12 multiblock

<400> SEQUENCE: 6

Gly His His His His His His Asn Gly Trp Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Gly Gly Lys Gly Gly Lys Gly Gly Lys
65                  70                  75                  80

Gly Gly Lys Gly Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Tyr
145

<210> SEQ ID NO 7
<211> LENGTH: 266
<212> TYPE: PRT
<213> ORGANISM: artificial
<220> FEATURE:
<223> OTHER INFORMATION: V24-K4-V24 multiblock

<400> SEQUENCE: 7

Gly His His His His His His Asn Gly Trp Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125
```

-continued

```
Gly Val Gly Gly Gly Lys Gly Gly Lys Gly Gly Lys Gly Gly Lys Gly
    130             135             140

Gly Val Pro Gly Val Gly Val Pro Gly Val Gly Val Pro Gly Val Gly
145             150             155             160

Val Pro Gly Val Gly Val Pro Gly Val Gly Val Pro Gly Val Gly Val
            165             170             175

Pro Gly Val Gly Val Pro Gly Val Gly Val Pro Gly Val Gly Val Pro
            180             185             190

Gly Val Gly Val Pro Gly Val Gly Val Pro Gly Val Gly Val Pro Gly
        195             200             205

Val Gly Val Pro Gly Val Gly Val Pro Gly Val Gly Val Pro Gly Val
    210             215             220

Gly Val Pro Gly Val Gly Val Pro Gly Val Gly Val Pro Gly Val Gly
225             230             235             240

Val Pro Gly Val Gly Val Pro Gly Val Gly Val Pro Gly Val Gly Val
            245             250             255

Pro Gly Val Gly Val Pro Gly Val Gly Tyr
            260             265

<210> SEQ ID NO 8
<211> LENGTH: 503
<212> TYPE: PRT
<213> ORGANISM: artificial
<220> FEATURE:
<223> OTHER INFORMATION: CryS96 (alpha B-crystallin peptide fused with
      ELP S96)

<400> SEQUENCE: 8

Gly Asp Arg Phe Ser Val Asn Leu Asp Val Lys His Phe Ser Pro Glu
1               5                   10                  15

Glu Leu Lys Val Lys Gly Val Pro Gly Ser Gly Val Pro Gly Ser Gly
            20                  25                  30

Val Pro Gly Ser Gly Val Pro Gly Ser Gly Val Pro Gly Ser Gly Val
            35                  40                  45

Pro Gly Ser Gly Val Pro Gly Ser Gly Val Pro Gly Ser Gly Val Pro
    50                  55                  60

Gly Ser Gly Val Pro Gly Ser Gly Val Pro Gly Ser Gly Val Pro Gly
65                  70                  75                  80

Ser Gly Val Pro Gly Ser Gly Val Pro Gly Ser Gly Val Pro Gly Ser
            85                  90                  95

Gly Val Pro Gly Ser Gly Val Pro Gly Ser Gly Val Pro Gly Ser Gly
            100             105             110

Val Pro Gly Ser Gly Val Pro Gly Ser Gly Val Pro Gly Ser Gly Val
        115             120             125

Pro Gly Ser Gly Val Pro Gly Ser Gly Val Pro Gly Ser Gly Val Pro
    130             135             140

Gly Ser Gly Val Pro Gly Ser Gly Val Pro Gly Ser Gly Val Pro Gly
145             150             155             160

Ser Gly Val Pro Gly Ser Gly Val Pro Gly Ser Gly Val Pro Gly Ser
            165             170             175

Gly Val Pro Gly Ser Gly Val Pro Gly Ser Gly Val Pro Gly Ser Gly
            180             185             190

Val Pro Gly Ser Gly Val Pro Gly Ser Gly Val Pro Gly Ser Gly Val
        195             200             205

Pro Gly Ser Gly Val Pro Gly Ser Gly Val Pro Gly Ser Gly Val Pro
```

```
          210                 215                 220

Gly Ser Gly Val Pro Gly Ser Gly Val Pro Gly Ser Gly Val Pro Gly
225                 230                 235                 240

Ser Gly Val Pro Gly Ser Gly Val Pro Gly Ser Gly Val Pro Gly Ser
                245                 250                 255

Gly Val Pro Gly Ser Gly Val Pro Gly Ser Gly Val Pro Gly Ser Gly
                260                 265                 270

Val Pro Gly Ser Gly Val Pro Gly Ser Gly Val Pro Gly Ser Gly Val
            275                 280                 285

Pro Gly Ser Gly Val Pro Gly Ser Gly Val Pro Gly Ser Gly Val Pro
        290                 295                 300

Gly Ser Gly Val Pro Gly Ser Gly Val Pro Gly Ser Gly Val Pro Gly
305                 310                 315                 320

Ser Gly Val Pro Gly Ser Gly Val Pro Gly Ser Gly Val Pro Gly Ser
                325                 330                 335

Gly Val Pro Gly Ser Gly Val Pro Gly Ser Gly Val Pro Gly Ser Gly
                340                 345                 350

Val Pro Gly Ser Gly Val Pro Gly Ser Gly Val Pro Gly Ser Gly Val
            355                 360                 365

Pro Gly Ser Gly Val Pro Gly Ser Gly Val Pro Gly Ser Gly Val Pro
        370                 375                 380

Gly Ser Gly Val Pro Gly Ser Gly Val Pro Gly Ser Gly Val Pro Gly
385                 390                 395                 400

Ser Gly Val Pro Gly Ser Gly Val Pro Gly Ser Gly Val Pro Gly Ser
                405                 410                 415

Gly Val Pro Gly Ser Gly Val Pro Gly Ser Gly Val Pro Gly Ser Gly
                420                 425                 430

Val Pro Gly Ser Gly Val Pro Gly Ser Gly Val Pro Gly Ser Gly Val
            435                 440                 445

Pro Gly Ser Gly Val Pro Gly Ser Gly Val Pro Gly Ser Gly Val Pro
        450                 455                 460

Gly Ser Gly Val Pro Gly Ser Gly Val Pro Gly Ser Gly Val Pro Gly
465                 470                 475                 480

Ser Gly Val Pro Gly Ser Gly Val Pro Gly Ser Gly Val Pro Gly Ser
                485                 490                 495

Gly Val Pro Gly Ser Gly Tyr
            500

<210> SEQ ID NO 9
<211> LENGTH: 173
<212> TYPE: PRT
<213> ORGANISM: artificial
<220> FEATURE:
<223> OTHER INFORMATION: V24-EGF

<400> SEQUENCE: 9

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
                20                  25                  30

Gly Val Gly Val Pro Gly Val Gly Val Pro Gly Val Gly Val Pro Gly
            35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
```

-continued

```
65                   70                   75                   80

Val Pro Gly Val Gly Val Pro Gly Val Gly Val Pro Gly Val Gly Val
                85                   90                   95

Pro Gly Val Gly Val Pro Gly Val Gly Val Pro Gly Val Gly Val Pro
            100                  105                  110

Gly Val Gly Val Pro Gly Val Gly Asn Ser Asp Ser Glu Cys Pro Leu
        115                  120                  125

Ser His Asp Gly Tyr Cys Leu His Asp Gly Val Cys Met Tyr Ile Glu
        130                  135                  140

Ala Leu Asp Lys Tyr Ala Cys Asn Cys Val Val Gly Tyr Ile Gly Glu
145                  150                  155                  160

Arg Cys Gln Tyr Arg Asp Leu Lys Trp Trp Glu Leu Arg
                165                  170

<210> SEQ ID NO 10
<211> LENGTH: 202
<212> TYPE: PRT
<213> ORGANISM: artificial
<220> FEATURE:
<223> OTHER INFORMATION: N8

<400> SEQUENCE: 10

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
            85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Tyr
        195                 200

<210> SEQ ID NO 11
<211> LENGTH: 202
<212> TYPE: PRT
<213> ORGANISM: artificial
<220> FEATURE:
<223> OTHER INFORMATION: A8

<400> SEQUENCE: 11
```

-continued

```
Gly Val Gly Val Pro Gly Ile Gly Val Pro Gly Ile Gly Val Pro Gly
1               5                   10                  15

Glu Gly Val Pro Gly Ile Gly Val Pro Gly Val Gly Val Pro Gly Ile
            20                  25                  30

Gly Val Pro Gly Ile Gly Val Pro Gly Glu Gly Val Pro Gly Ile Gly
        35                  40                  45

Val Pro Gly Val Gly Val Pro Gly Ile Gly Val Pro Gly Ile Gly Val
    50                  55                  60

Pro Gly Glu Gly Val Pro Gly Ile Gly Val Pro Gly Val Gly Val Pro
65                  70                  75                  80

Gly Ile Gly Val Pro Gly Ile Gly Val Pro Gly Glu Gly Val Pro Gly
                85                  90                  95

Ile Gly Val Pro Gly Val Gly Val Pro Gly Ile Gly Val Pro Gly Ile
            100                 105                 110

Gly Val Pro Gly Glu Gly Val Pro Gly Ile Gly Val Pro Gly Val Gly
        115                 120                 125

Val Pro Gly Ile Gly Val Pro Gly Ile Gly Val Pro Gly Glu Gly Val
    130                 135                 140

Pro Gly Ile Gly Val Pro Gly Val Gly Val Pro Gly Ile Gly Val Pro
145                 150                 155                 160

Gly Ile Gly Val Pro Gly Glu Gly Val Pro Gly Ile Gly Val Pro Gly
            165                 170                 175

Val Gly Val Pro Gly Ile Gly Val Pro Gly Ile Gly Val Pro Gly Glu
            180                 185                 190

Gly Val Pro Gly Ile Gly Val Pro Gly Tyr
        195                 200
```

```
<210> SEQ ID NO 12
<211> LENGTH: 402
<212> TYPE: PRT
<213> ORGANISM: artificial
<220> FEATURE:
<223> OTHER INFORMATION: A16

<400> SEQUENCE: 12
```

```
Gly Val Gly Val Pro Gly Ile Gly Val Pro Gly Ile Gly Val Pro Gly
1               5                   10                  15

Glu Gly Val Pro Gly Ile Gly Val Pro Gly Val Gly Val Pro Gly Ile
            20                  25                  30

Gly Val Pro Gly Ile Gly Val Pro Gly Glu Gly Val Pro Gly Ile Gly
        35                  40                  45

Val Pro Gly Val Gly Val Pro Gly Ile Gly Val Pro Gly Ile Gly Val
    50                  55                  60

Pro Gly Glu Gly Val Pro Gly Ile Gly Val Pro Gly Val Gly Val Pro
65                  70                  75                  80

Gly Ile Gly Val Pro Gly Ile Gly Val Pro Gly Glu Gly Val Pro Gly
                85                  90                  95

Ile Gly Val Pro Gly Val Gly Val Pro Gly Ile Gly Val Pro Gly Ile
            100                 105                 110

Gly Val Pro Gly Glu Gly Val Pro Gly Ile Gly Val Pro Gly Val Gly
        115                 120                 125

Val Pro Gly Ile Gly Val Pro Gly Ile Gly Val Pro Gly Glu Gly Val
    130                 135                 140

Pro Gly Ile Gly Val Pro Gly Val Gly Val Pro Gly Ile Gly Val Pro
145                 150                 155                 160
```

-continued

```
Gly Ile Gly Val Pro Gly Glu Gly Val Pro Gly Ile Gly Val Pro Gly
                165                 170                 175

Val Gly Val Pro Gly Ile Gly Val Pro Gly Ile Gly Val Pro Gly Glu
            180                 185                 190

Gly Val Pro Gly Ile Gly Val Pro Gly Val Gly Val Pro Gly Ile Gly
        195                 200                 205

Val Pro Gly Ile Gly Val Pro Gly Glu Gly Val Pro Gly Ile Gly Val
    210                 215                 220

Pro Gly Val Gly Val Pro Gly Ile Gly Val Pro Gly Ile Gly Val Pro
225                 230                 235                 240

Gly Glu Gly Val Pro Gly Ile Gly Val Pro Gly Val Gly Val Pro Gly
            245                 250                 255

Ile Gly Val Pro Gly Ile Gly Val Pro Gly Glu Gly Val Pro Gly Ile
            260                 265                 270

Gly Val Pro Gly Val Gly Val Pro Gly Ile Gly Val Pro Gly Ile Gly
        275                 280                 285

Val Pro Gly Glu Gly Val Pro Gly Ile Gly Val Pro Gly Val Gly Val
    290                 295                 300

Pro Gly Ile Gly Val Pro Gly Ile Gly Val Pro Gly Glu Gly Val Pro
305                 310                 315                 320

Gly Ile Gly Val Pro Gly Val Gly Val Pro Gly Ile Gly Val Pro Gly
            325                 330                 335

Ile Gly Val Pro Gly Glu Gly Val Pro Gly Ile Gly Val Pro Gly Val
            340                 345                 350

Gly Val Pro Gly Ile Gly Val Pro Gly Ile Gly Val Pro Gly Glu Gly
        355                 360                 365

Val Pro Gly Ile Gly Val Pro Gly Val Gly Val Pro Gly Ile Gly Val
    370                 375                 380

Pro Gly Ile Gly Val Pro Gly Glu Gly Val Pro Gly Ile Gly Val Pro
385                 390                 395                 400

Gly Tyr
```

```
<210> SEQ ID NO 13
<211> LENGTH: 802
<212> TYPE: PRT
<213> ORGANISM: artificial
<220> FEATURE:
<223> OTHER INFORMATION: A32

<400> SEQUENCE: 13

Gly Val Gly Val Pro Gly Ile Gly Val Pro Gly Ile Gly Val Pro Gly
1               5                   10                  15

Glu Gly Val Pro Gly Ile Gly Val Pro Gly Val Gly Val Pro Gly Ile
            20                  25                  30

Gly Val Pro Gly Ile Gly Val Pro Gly Glu Gly Val Pro Gly Ile Gly
        35                  40                  45

Val Pro Gly Val Gly Val Pro Gly Ile Gly Val Pro Gly Ile Gly Val
    50                  55                  60

Pro Gly Glu Gly Val Pro Gly Ile Gly Val Pro Gly Val Gly Val Pro
65                  70                  75                  80

Gly Ile Gly Val Pro Gly Ile Gly Val Pro Gly Glu Gly Val Pro Gly
                85                  90                  95

Ile Gly Val Pro Gly Val Gly Val Pro Gly Ile Gly Val Pro Gly Ile
            100                 105                 110

Gly Val Pro Gly Glu Gly Val Pro Gly Ile Gly Val Pro Gly Val Gly
```

-continued

```
              115                 120                 125

Val Pro Gly Ile Gly Val Pro Gly Ile Gly Val Pro Gly Glu Gly Val
    130                 135                 140

Pro Gly Ile Gly Val Pro Gly Val Gly Val Pro Gly Ile Gly Val Pro
145                 150                 155                 160

Gly Ile Gly Val Pro Gly Glu Gly Val Pro Gly Ile Gly Val Pro Gly
                165                 170                 175

Val Gly Val Pro Gly Ile Gly Val Pro Gly Ile Gly Val Pro Gly Glu
                180                 185                 190

Gly Val Pro Gly Ile Gly Val Pro Gly Val Gly Val Pro Gly Ile Gly
                195                 200                 205

Val Pro Gly Ile Gly Val Pro Gly Glu Gly Val Pro Gly Ile Gly Val
    210                 215                 220

Pro Gly Val Gly Val Pro Gly Ile Gly Val Pro Gly Ile Gly Val Pro
225                 230                 235                 240

Gly Glu Gly Val Pro Gly Ile Gly Val Pro Gly Val Gly Val Pro Gly
                245                 250                 255

Ile Gly Val Pro Gly Ile Gly Val Pro Gly Glu Gly Val Pro Gly Ile
                260                 265                 270

Gly Val Pro Gly Val Gly Val Pro Gly Ile Gly Val Pro Gly Ile Gly
                275                 280                 285

Val Pro Gly Glu Gly Val Pro Gly Ile Gly Val Pro Gly Val Gly Val
    290                 295                 300

Pro Gly Ile Gly Val Pro Gly Ile Gly Val Pro Gly Glu Gly Val Pro
305                 310                 315                 320

Gly Ile Gly Val Pro Gly Val Gly Val Pro Gly Ile Gly Val Pro Gly
                325                 330                 335

Ile Gly Val Pro Gly Glu Gly Val Pro Gly Ile Gly Val Pro Gly Val
                340                 345                 350

Gly Val Pro Gly Ile Gly Val Pro Gly Ile Gly Val Pro Gly Glu Gly
                355                 360                 365

Val Pro Gly Ile Gly Val Pro Gly Val Gly Val Pro Gly Ile Gly Val
    370                 375                 380

Pro Gly Ile Gly Val Pro Gly Glu Gly Val Pro Gly Ile Gly Val Pro
385                 390                 395                 400

Gly Val Gly Val Pro Gly Ile Gly Val Pro Gly Ile Gly Val Pro Gly
                405                 410                 415

Glu Gly Val Pro Gly Ile Gly Val Pro Gly Val Gly Val Pro Gly Ile
                420                 425                 430

Gly Val Pro Gly Ile Gly Val Pro Gly Glu Gly Val Pro Gly Ile Gly
                435                 440                 445

Val Pro Gly Val Gly Val Pro Gly Ile Gly Val Pro Gly Ile Gly Val
    450                 455                 460

Pro Gly Glu Gly Val Pro Gly Ile Gly Val Pro Gly Val Gly Val Pro
465                 470                 475                 480

Gly Ile Gly Val Pro Gly Ile Gly Val Pro Gly Glu Gly Val Pro Gly
                485                 490                 495

Ile Gly Val Pro Gly Val Gly Val Pro Gly Ile Gly Val Pro Gly Ile
                500                 505                 510

Gly Val Pro Gly Glu Gly Val Pro Gly Ile Gly Val Pro Gly Val Gly
                515                 520                 525

Val Pro Gly Ile Gly Val Pro Gly Ile Gly Val Pro Gly Glu Gly Val
    530                 535                 540
```

-continued

```
Pro Gly Ile Gly Val Pro Gly Val Gly Val Pro Gly Ile Gly Val Pro
545                 550                 555                 560

Gly Ile Gly Val Pro Gly Glu Gly Val Pro Gly Ile Gly Val Pro Gly
                565                 570                 575

Val Gly Val Pro Gly Ile Gly Val Pro Gly Ile Gly Val Pro Gly Glu
            580                 585                 590

Gly Val Pro Gly Ile Gly Val Pro Gly Val Gly Val Pro Gly Ile Gly
            595                 600                 605

Val Pro Gly Ile Gly Val Pro Gly Glu Gly Val Pro Gly Ile Gly Val
    610                 615                 620

Pro Gly Val Gly Val Pro Gly Ile Gly Val Pro Gly Ile Gly Val Pro
625                 630                 635                 640

Gly Glu Gly Val Pro Gly Ile Gly Val Pro Gly Val Gly Val Pro Gly
                645                 650                 655

Ile Gly Val Pro Gly Ile Gly Val Pro Gly Glu Gly Val Pro Gly Ile
            660                 665                 670

Gly Val Pro Gly Val Gly Val Pro Gly Ile Gly Val Pro Gly Ile Gly
            675                 680                 685

Val Pro Gly Glu Gly Val Pro Gly Ile Gly Val Pro Gly Val Gly Val
    690                 695                 700

Pro Gly Ile Gly Val Pro Gly Ile Gly Val Pro Gly Glu Gly Val Pro
705                 710                 715                 720

Gly Ile Gly Val Pro Gly Val Gly Val Pro Gly Ile Gly Val Pro Gly
                725                 730                 735

Ile Gly Val Pro Gly Glu Gly Val Pro Gly Ile Gly Val Pro Gly Val
            740                 745                 750

Gly Val Pro Gly Ile Gly Val Pro Gly Ile Gly Val Pro Gly Glu Gly
            755                 760                 765

Val Pro Gly Ile Gly Val Pro Gly Val Gly Val Pro Gly Ile Gly Val
    770                 775                 780

Pro Gly Ile Gly Val Pro Gly Glu Gly Val Pro Gly Ile Gly Val Pro
785                 790                 795                 800

Gly Tyr

<210> SEQ ID NO 14
<211> LENGTH: 5
<212> TYPE: PRT
<213> ORGANISM: Artificial
<220> FEATURE:
<223> OTHER INFORMATION: Tropoelastine Pentapeptide Unit

<400> SEQUENCE: 14

Val Pro Gly Val Gly
1               5

<210> SEQ ID NO 15
<211> LENGTH: 5
<212> TYPE: PRT
<213> ORGANISM: artificial
<220> FEATURE:
<223> OTHER INFORMATION: Synthetic ELP Pentapeptide Repeat Unit
<220> FEATURE:
```

-continued

```
<221> NAME/KEY: X
<222> LOCATION: (4)..(4)
<223> OTHER INFORMATION: X is any amino acid other than proline

<400> SEQUENCE: 15

Val Pro Gly Xaa Gly
1               5
```

RAPID AND SIMPLE PURIFICATION OF ELASTIN-LIKE POLYPEPTIDES DIRECTLY FROM WHOLE CELLS AND CELL LYSATES BY ORGANIC SOLVENT EXTRACTION

CROSS REFERENCE TO RELATED APPLICATIONS

This U.S. patent application is a national stage entry under 35 U.S.C. § 371(b) of International Application No. PCT/US2019/19468, filed Feb. 25, 2019, which is related to and claims the priority benefit of U.S. Provisional Patent Application No. 62/635,309, filed on Feb. 26, 2018. The contents of which are expressly incorporated herein entirely by reference.

GOVERNMENT SUPPORT

This invention was made with government support under contract number CA023168 awarded by the National Institutes of Health. The government has certain rights in the invention.

SEQUENCE LISTING

A computer-readable form (CRF) of the Sequence Listing is submitted with this application and incorporated herein by reference. The Sequence Listing file entitled 68157-03_SEQ LISTING ST25.txt (36000 bytes) is generated on Jul. 31, 2024. Applicant states that the sequence listing in computer-readable form (.txt file) provides the same information as the sequence listing written in the specification.

FIELD OF INVENTION

This application relates to a method of fast purifying elastin-like polypeptides directly from whole cell lysates. Particularly, any peptides expressed with elastin-like polypeptides tags can be purified using the disclosed organic solvent extraction to achieve high yields within minutes.

BACKGROUND

Elastin-like polypeptides (ELP) represent a class of proteins derived from mammalian elastin, also commonly referred to as tropoelastin (TEL). TEL is composed of many repeating hydrophilic and hydrophobic domains, with the pentapeptide unit VPGVG [SEQ ID No:14] being the most prevalent hydrophobic unit. Synthetic ELP are based on a related pentapeptide repeat, VPGXG [SEQ ID No:15], where X is a guest residue that may be any amino acid except proline. The hallmark feature of ELP is their intrinsic lower critical solution temperature (LCST) in water, where heating the solution to a certain threshold temperature drives hydrophobic collapse and reversible ELP coacervation. Urry et al. established the biophysical understanding of this so-called inverse transition temperature ($T_t$). This critical temperature is highly dependent on numerous intrinsic factors, including ELP molecular weight and guest residue hydrophobicity, and external factors, such as pH, ELP concentration, and salt composition.

In addition to the appealing feature of a tunable $T_t$, ELP offer several additional benefits that make them highly attractive materials in biomedical and therapeutic applications. For example, they can be imbued with unique functionality, such as targeting peptides or sites for chemical modification via genetic manipulation. Additionally, ELP have shown beneficial stealth-like and pharmacokinetic properties comparable to PEGylation, while being biodegradable and non-immunogenic. A variety of applications, including targeted delivery mediated by targeting peptides and local hyperthermia, size-controlled nanoparticle formation, small molecule drug and vaccine delivery vehicles, tissue engineering, anti-fouling coatings, and underwater adhesives have been reported using ELP constructs.

As an alternative to commonly used affinity or size-exclusion chromatography methods, ELP can be uniquely purified non-chromatographically by exploiting their inherent $T_t$. ELP can also be utilized as a purification tag for fusion protein isolation. The Chilkoti group pioneered this relatively simple purification process, known as inverse transition cycling (ITC), wherein a clarified lysate containing an ELP or ELP-fusion is transitioned above its $T_t$, isolated from the soluble contaminants by centrifugation, re-dissolved in cold aqueous solution, and centrifuged again to remove insoluble contaminants. Repeating this cycle multiple times increases ELP purity. In many cases, a highly pure ELP can be isolated in less than a day by performing 2-5 rounds of ITC; however, each round also diminishes the total yield of the purified material.

Despite the vast number of publications describing ITC as an ELP purification method, the process has severe inherent limitations in some cases. For example, non-protein macromolecular contaminants, such as nucleic acids, can be problematic for the ITC process and are commonly co-purified with the target ELP. Although a nucleic acid precipitation step with branched polyethylenimine (bPEI) is often effective before ITC, it increases the processing cost and time, as well as being incompatible with certain ELP constructs.

In addition, the utility of ITC is limited only to ELP exhibiting convenient transition temperatures. Some constructs in this range still do not transition strongly and, subsequently, purify poorly by ITC. This limit is primarily governed by the overall hydrophobicity and molecular weight of the ELP construct. For very hydrophobic guest residues (or fusion proteins) and high molecular weight ELP, the $T_t$ falls below 20° C. and becomes experimentally difficult. Low-expressing ELP, hydrophilic inclusions, and very low molecular weight ELP that exhibit transition temperatures too high to reasonably reach in aqueous solution, even when including salts to lower the $T_t$, are examples of other experimentally challenging cases. Since ITC, due to its unique specificity and simplicity is typically the preferred method for ELP purification, ELP found in the literature are rarely at the extremes of hydrophobicity/hydrophilicity or molecular weight ranges.

Therefore, there remains a need of identifying more suitable approach of purifying ELPs in a timely fashion.

SUMMARY OF THE INVENTION

Elastin-like polypeptides (ELP) are increasingly utilized for their beneficial physicochemical properties. A unifying feature of ELP is their demonstration of a sequence tunable inverse transition temperature ($T_t$) and as such, ELP can often be easily purified using a simple, straightforward process called inverse transition cycling (ITC). ITC has led to the successful purification of a vast number of ELP constructs and has resulted in ELP being used as purification tags for isolating other proteins of interests. Despite the utility of ITC, the process is inherently limited to ELP with an experimentally accessible $T_t$.

In this application we utilized ELP's overall hydrophobicity and procure ELPs as excellent candidates for purification by organic extraction. We report the first method for rapidly purifying ELP or ELP fusion proteins directly from whole *E. coli* cells or clarified lysates. Our results show that small ELP and a large ELP-fusion protein can be isolated in high yield from whole cells or cell lysates with greater than 95% purity in less than 30 min.

This disclosure provides a method to purify Elastin like polypeptides (ELPs) from a total cell lysate. The method comprising the steps of:

a. Preparing a clarified cell lysate, wherein said cell lysate comprising at least one ELP with or without fusing to other proteins;
    b. Preparing at least one organic extractant;
    c. Adding said cell lysate to the organic extractant;
    d. Vortexing the mixture before subjecting the mixture to centrifugation; and
    e. Selectively recovering the upper organic phase that comprises the at least one ELP with or without fusing to other proteins.

In some embodiment, the aforementioned method further comprising adding an aqueous salt solution to the recovered organic phase of extractant, and repeating steps d and e.

In some embodiment, the aforementioned method further comprising laying the organic extractant on top of an aqueous salt solution before step c.

This disclosure further provides a method to purify Elastin like polypeptides (ELPs) from whole cells that express at least one ELP with or without fusing to other proteins. The method comprising the steps of:

a. Preparing whole cell pellets;
    b. Mixing an organic solvent with the whole cell pellets to form a first mixture;
    c. Vertexing the first mixture before subjecting the first mixture to centrifugation until a first organic phase is formed;
    d. Selectively collecting the first organic phase;
    e. Adding anti-solvent and water to the collected organic phase to form a second mixture;
    f. Subjecting the second mixture to centrifugation until an aqueous phase and a second organic phase are formed; and
    g. Removing the second organic phase to recover the purified (back-extracted) ELP in the aqueous phase.

This disclosure further provides a method to purify Elastin like polypeptides (ELPs) from whole cells that express at least one ELP with or without fusing to other proteins. The method comprising:

a. Preparing whole cell pellets;
    b. Mixing an organic solvent with said whole cell pellets to form a first mixture;
    c. Vortexing the first mixture before subjecting to centrifugation until a first organic phase is formed;
    d. Selectively collecting the first organic phase;
    e. Adding acetonitrile to the collected organic phase to form a second mixture;
    f. Subjecting the second mixture to centrifugation until a pellet and a second organic phase are formed;
    g. Removing the second organic phase to recover the pelleted (precipitated) ELP and placing it back in an aqueous phase solution; and
    h. Subjecting the aqueous phase solution to centrifugation to remove contaminants and recovering ELP in aqueous phase by collecting supernatant.

In some preferred embodiments, the aforementioned methods are to purify ELPs selected from the group consisting of SEQ ID Nos: 3-13 (V12, V24, S12-$K_4$-S12, V12-$K_4$-V12, V24-$K_4$-V24, CryS96, V24-EGF, N8, A8, A16, and A32, respectively).

In some preferred embodiment, the aforementioned organic extractant or organic solvent is selected from the group consisting of IPA, nBuOH, EtOAc, Ace, ACN, EtOH and MeOH, or the combination thereof.

In some preferred embodiment, the aforementioned organic solvents in combination has a ratio of about 1:1.

In some preferred embodiment, the aforementioned recovered ELP is substantially nucleic acid free.

In some preferred embodiment, the aforementioned recovered ELP is substantially lipopolysaccharide (LPS) free.

In some preferred embodiment, the aforementioned methods of ELP purification considerably reduce purification time compared to the conventional inverse transition cycling (ITC) method.

These and other features, aspects and advantages of the present invention will become better understood with reference to the following figures, associated descriptions and claims.

Back Extraction—A liquid extraction was performed on the supernatant from the polar organic extraction. 2 times the ethyl acetate was added to the organic solvent blend (v/v). The mixture was briefly mixed, vented and spun at 6000×g for 5 minutes. The layers were then separated using a serological pipette. The bottom layer was evaporated, resuspended in PBS, 1 times the weight of pellet (w/v) and loaded on gel (well4). Another same case was followed by hot spin (well5)

ACN or Ace precipitation—Samples were precipitated by adding 100 percent acetone or acetonitrile till final volume is 70% v/v.

C2 centrifugation—Solution was centrifuged (8000×g, 15 mins) and supernatant was discarded, pellet was resuspended in PBS unless otherwise stated. (well6) Another sample underwent hot spin and was loaded on well 7

Hot Spin—Sample was heated to 37° C. and saturated ammonium sulfate was added to the solution to a final concentration of 20% v/v. The solution was spun down at 13000×g for 20 mins at 40° C. The supernatant decanted and the pellet resuspended in PBS on ice unless otherwise stated.

Cold Spin—The resuspended hot spin pellet was cooled at 4° C. and spun at 10000×g, 15 mins at 4° C. The supernatant was decanted into a new tube.

Back Extraction—A liquid extraction was performed on the supernatant from the polar organic extraction. 3 times the ethyl acetate was added to the organic solvent blend (v/v). The mixture was briefly mixed, vented and spun at 6000×g for 10 minutes. The layers were then separated using a serological pipette.

Cell lysis by sonication—An *E. coli* cell pellet was resuspended in 4 times it weight in PBS. The slurry was then incubated with lysozyme at a concentration of 0.1 mg/mL. The slurry was probe tip sonicated for 30 minutes at a 30% duty cycle. Centrifugation at 13000×g for 40 minutes clarified the sample. Lysate was loaded on well8, after one round of ITC-well9 and after 3 rounds of ITC-well10.

Figure 34:
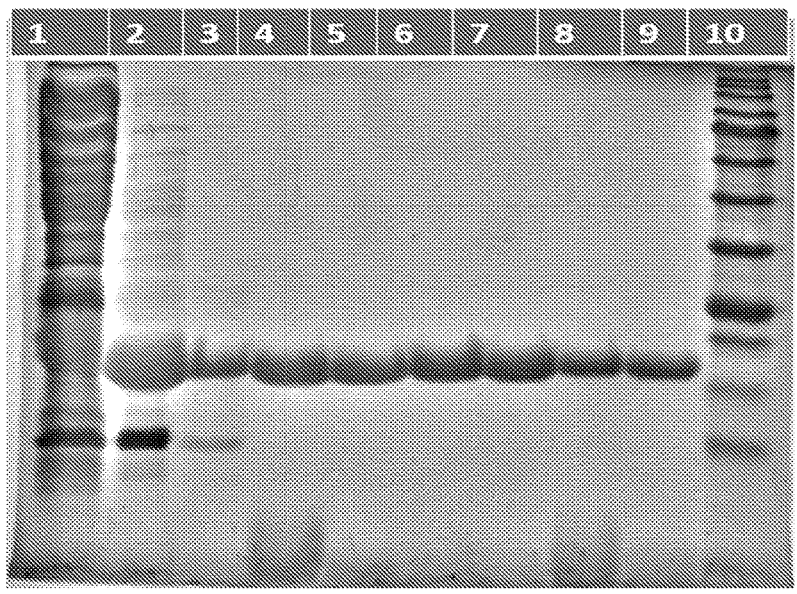

FIG. 34. A8 various purification. Polar Organic Extraction: An *E. coli* cell pellet was extracted with 4 times the bacterial pellet weight (w/v) with a IPA:BuOH (1:1) mixture by adding the organic solvent blend and vortexing for a minute unless otherwise stated. The slurry is spun down (10000×g, 15 mins) to remove the insoluble cell debris and the supernatant is collected by decanting into a new tube. A sample was taken and evaporated and resuspended in PBS 1 time w/v of the pellet (well4). Another sample underwent a round of hot spin and was loaded in well5.

Back Extraction—A liquid extraction was performed on the supernantant from the polar organic extraction. 2 times the ethyl acetate was added to the organic solvent blend (v/v). The mixture was briefly mixed, vented and spun at 6000×g for 5 minutes. The layers were then separated using a serological pipette. The bottom layer was evaporated, resuspended in PBS, 1 times the weight of pellet (w/v) and loaded on gel (well6). Another same case was followed by hot spin (well7)

ACN or Ace precipitation—Samples were precipitated by adding 100 percent acetone or acetonitrile till final volume is 70% v/v.

C2 centrifugation—Solution was centrifuged (8000×g, 15 mins) and supernatant was discarded, pellet was resuspended in PBS unless otherwise stated. (well8) Another sample underwent hot spin and was loaded on well 9.

Hot Spin—Sample was heated to 37° C. and saturated ammonium sulfate was added to the solution to a final concentration of 20% v/v. The solution was spun down at 13000×g for 20 mins at 40° C. The supernatant decanted and the pellet resuspended in PBS on ice unless otherwise stated.

Cold Spin—The resuspended hot spin pellet was cooled at 4° C. and spun at 10000×g, 15 mins at 4° C. The supernatant was decanted into a new tube.

Cell lysis by sonication—An *E. coli* cell pellet was resuspended in 4 times it weight in PBS. The slurry was then incubated with lysozyme at a concentration of 0.1 mg/mL. The slurry was probe tip sonicated for 30 minutes at a 30% duty cycle. Centrifugation at 13000×g for 40 minutes clarified the sample. Lysate was loaded on well1, after one round of ITC-well2 and after 3 rounds of hot spin-well3.

Figure 35:
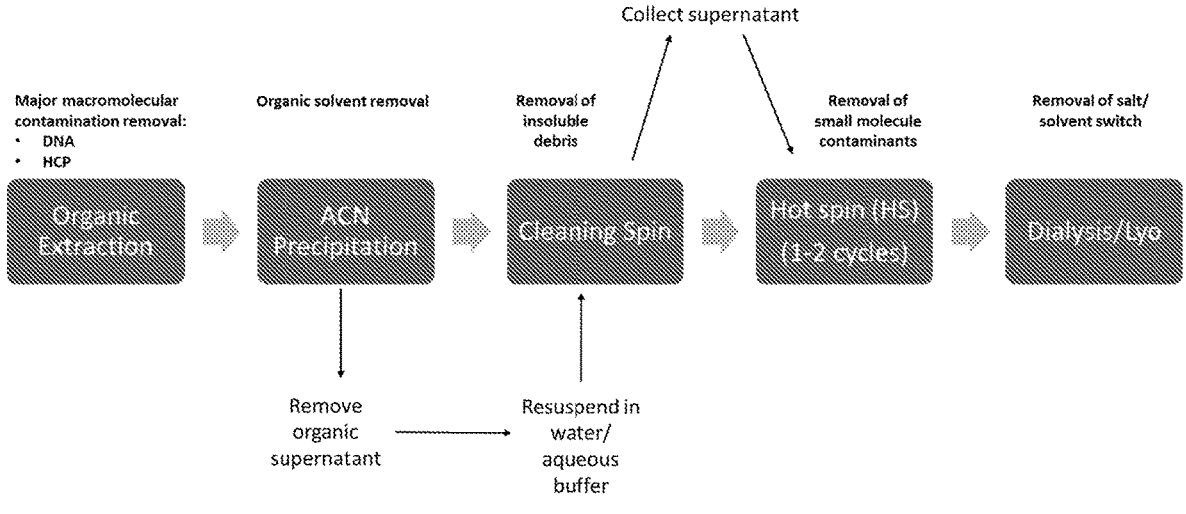

FIG. 35. Optimized Elastin-like Peptide Purification Scheme.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Non-chromatographic protein purification methods, other than ITC, are rare. Purification by organic extraction; however, has been utilized for a handful of proteins with unique physicochemical properties. Of particular interest, Yakhnin and coworkers recognized an opportunity for exploiting the highly hydrophobic properties of green fluorescent protein (GFP) and described the first extraction method for GFP purification from bacterial cell lysates. This simple two-step method was further optimized for GFP and a number of similar fluorescent variants, offering 70% recovery and purity exceeding 95% in less than an hour.

Similarly, Sandberg and coworkers recognized the hydrophobicity of tropoelastin and developed a complex extraction method for recovering soluble TEL from tissue samples. While other methods are typically preferred today for TEL recovery, this procedure has been used to extract elastin from bovine tissues and a modified method successfully purified TEL from *E. coli* lysates. Using a mixture of n-propanol and n-butanol, an estimated yield of 90% TEL was recovered from lysate, with minimal non-target protein contamination. Although effective and relatively fast, this process still takes several hours to complete.

Without being limited by any theory, we hypothesized that intrinsically hydrophobic ELP and ELP-fusions may be rapidly isolated in high purity via organic solvent extraction. Further, due to the destabilizing nature of organic solvents on bacterial cells (e.g., *E. coli*), we anticipated that a single step could simultaneously lyse the expression cells and selectively extract the target ELP without nucleic acid contamination. Herein, we describe a set of organic extraction procedures for rapid recovery of extremely pure ELP and an ELP-fusion directly from whole cells and cell lysates with little or no contamination by nucleic acids or lipopolysaccharides.

Organic extraction has been demonstrated as an extremely rapid and efficient method for the scalable purification of ELP directly from whole cells or cell lysates, requiring less than 30 min in either case. We have shown that the optimized extraction process is highly efficient in removing contaminating nucleic acids, non-target proteins, and lipopolysaccharides in a single step and may be optimized for ELP sequences differing widely in molecular weight, hydrophobicity, or the presence of non-ELP fusions. In the case of direct extraction from whole cells, it is possible to recover more isolated target protein than the amount of crude target protein liberated by some standard lysis methods. Utilizing organic extraction, we anticipate that many other ELP constructs, especially those difficult to obtain by traditional methods, will become accessible by expression in bacteria without the need for purification tags. The ability to retain biological activity with CryS96 shows that organic extraction is an alternative means for protein purification while retaining the functionality of the fusion domain.

To our knowledge, the occurrence of other small molecule and metabolite contaminants in ITC-purified ELP has not been investigated. A variety of these contaminants may be carried along by the extraction process reported herein. Indeed, the contaminant profile is expected to be greatly dependent on the extractant employed. Numerous simple techniques such as gel filtration or dialysis are available for removing these low molecular weight contaminants. A second extraction, such as aqueous back-extraction or an additional organic extraction might also be effective in removing certain classes of contaminants. Alternatively, ACN precipitation or a round of ITC may be the most expedient method for removing a broader range of small molecules.

Although the newly-described method of purifying ELP by organic extraction has proven successful in many cases, additional experimentation is needed fully understand the mechanism of this process and a more in-depth analysis of the contaminant profile. The extraction mechanism is likely to depend on the specific combination of ELP and extractant. Employing a larger library of ELP constructs and organic solvents may be useful in understanding the extraction mechanism such that one could rationally predict extractability by relating ELP and solvent properties.

The disclosed extraction method will avoid using promiscuous solvents like MeOH and explore additional solvents, as necessary for other ELP constructs. A broad solvent screen may identify the most useful extractants that retain function for downstream applications. The method at least has the following advantages:

Identifying ideal extractant based on the application needs—a balance between yield, purity, and contaminant profile can be established.

Extraction target peptides/fusion proteins from whole cells, especially for labile proteins susceptible to enzymatic degradation. This is also a simpler process and does not require optimizing cell lysis conditions.

The order of the processing steps and timing also deserve attention to achieve the highest consistency in extraction outcomes.

Materials and Methods

Materials

All organic solvents were of high grade from either Fisher Scientific or Sigma Aldrich and used without additional purification or drying. Unless otherwise noted, water was ultra-filtered. All media for bacterial cell culture was autoclaved prior to use and contained an appropriate antibiotic. DNA sequences for gene assembly were purchased from IDT; restriction enzymes and bacterial cells were from NEB.

Synthesis of ELP Construct Genes

ELP genes were assembled using recursive directional ligation (RDL) techniques to iteratively assemble DNA block sequences. Final gene constructs were sequence-verified and transformed into BL21(DE3) E. coli for expression.

```
                 Protein Sequences
GFP (green fluorescent protein, UV variant
with an N-terminal polyhistidine tag)
                               SEQ ID NO: 1
SKGEELFTGV VPILVELDGD VNGHKFSVSG EGEGDATYGK

LTLKFICTTG KLPVPWPTLV TTFSYGVQCF SRYPDHMKRH

DFFKSAMPEG YVQERTISFK DDGNYKTRAE VKFEGDTLVN

RIELKGIDFK EDGNILGHKL EYNYNSHNVY ITADKQKNGI

KANFKIRHNI EDGSVQLADH YQQNTPIGDG PVLLPDNHYL

STQSKLSKDP NEKRDHMVLL EFVTAAGITH GMDELYKHHH HHHHH

TEL (human tropoelastin, main chain)
                               SEQ ID NO: 2
GGVPGAVPGG VPGGVFFPGA GLGGLGVGGL GPGVKPAKPG
```

```
                 -continued

Protein Sequences

VGGLVGPGLG AEGSALPGAF PGGFFGAGGG AAGAAAAYKA

AAKAGAAGLG VGGIGGVGGL GVSTGAVVPQ LGAGVGAGVK

PGKVPGVGLP GVYPGGVLPG AGARFPGIGV LPGVPTGAGV

KPKAQVGAGA FAGIPGVGPF GGQQPGLPLG YPIKAPKLPA

GYGLPYKTGK LPYGFGPGGV AGSAGKAGYP TGTGVGPQAA

AAAAKAAAKL GAGGAGVLPG VGVGGPGIPG APGAIPGIGG

IAGVGAPDAA AAAAAAAKAA KFGAAGGLPG VGVPGVGVPG

VGVPGVGVPG VGVPGVGVPG VGVPGVGVPG VGVPGVGVPG

VGVPGALSPA ATAKAAAKAA KFGARGAVGI GGIPTFGLGP

GGFPGIGDAA AAPAAAAAKA AKIGAGGVGA LGGVVPGAPG

AIPGLPGVGG VPGVGIPAAA AAKAAAKAAQ FGLGPGVGVA

PGVGVVPGVG VVPGVGVAPG IGLGPGGVIG AGVPAAAKSA

AKAAAKAQFR AAAGLPAGVP GLGVGAGVPG LGVGAGVPGL

GVGAGVPGPG AVPGTLAAAK AAKFGPGGVG ALGGVGDLGG

AGIPGGVAGV VPAAAAAKA AAKAAQFGLG GVGGLGVGGL

GAVPGAVGLG GVSPAAAAKA AKFGAAGLGG VLGAGQPFPI

GGGAGGLGVG GKPPKPFGGA LGALGFPGGA CLGKSCGRKR K

V12
                                   SEQ ID NO: 3
VPGVGVPGVG VPGVGVPGVG VPGVGVPGVG VPGVGVPGVG

VPGVGVPGVG VPGVGVPGVG Y

V24
                                   SEQ ID NO: 4
VPGVGVPGVG VPGVGVPGVG VPGVGVPGVG VPGVGVPGVG

VPGVGVPGVG VPGVGVPGVG VPGVGVPGVG VPGVGVPGVG

VPGVGVPGVG VPGVGVPGVG VPGVGVPGVG VPGVGVPGVG Y

S12-K4-S12
                                   SEQ ID NO: 5
GHHHHHHNGW GVPGSGVPGS GVPGSGVPGS GVPGSGVPGS

GVPGSGVPGS GVPGSGVPGS GVPGSGVPGS GGGKGGKGGK

GGKGGVPGSG VPGSGVPGSG VPGSGVPGSG VPGSGVPGSG

VPGSGVPGSG VPGSGVPGSG VPGSGY

V12-K4-V12
                                   SEQ ID NO: 6
GHHHHHHNGW GVPGVGVPGV GVPGVGVPGV GVPGVGVPGV

GVPGVGVPGV GVPGVGVPGV GVPGVGVPGV GGGKGGKGGK

GGKGGVPGVG VPGVGVPGVG VPGVGVPGVG VPGVGVPGVG

VPGVGVPGVG VPGVGVPGVG VPGVGY

V24-K4-V24
                                   SEQ ID NO: 7
GHHHHHHNGW GVPGVGVPGV GVPGVGVPGV GVPGVGVPGV

GVPGVGVPGV GVPGVGVPGV GVPGVGVPGV GVPGVGVPGV

GVPGVGVPGV GVPGVGVPGV GVPGVGVPGV GVPGVGVPGV

GVPGVGVPGV GGGKGGKGGK GGKGGVPGVG VPGVGVPGVG
```

-continued

```
Protein Sequences
```

VPGVGVPGVG VPGVGVPGVG VPGVGVPGVG VPGVGVPGVG

VPGVGVPGVG VPGVGVPGVG VPGVGVPGVG VPGVGVPGVG

VPGVGVPGVG VPGVGVPGVG VPGVGY

CryS96 (αB-crystallin peptide fused with ELP S96)
SEQ ID NO: 8
GDRFSVNLDV KHFSPEELKV KGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGVPGSGVPG SGVPGSGVPG

SGVPGSGVPG SGVPGSGVPG SGY

Additional Amino acid sequences: ( )$_n$ represent
repeats of bracketed amino acids
V24-EGF
SEQ ID NO: 9
(VPGVG)$_{24}$-

NSDSECPLSHDGYCLHDGVCMYIEALDKYACNCVVGYIGERCQY

RDLKWWELR

N8
SEQ ID NO: 10
(GVGVPGVGVPGVGVPGVGVPGVGVP)$_8$GY

A8
SEQ ID NO: 11
(GVGVPGIGVPGIGVPGEGVPGIGVP)$_8$GY

A16
SEQ ID NO: 12
(GVGVPGIGVPGIGVPGEGVPGIGVP)$_{16}$GY

A32
SEQ ID NO: 13
(GVGVPGIGVPGIGVPGEGVPGIGVP)$_{32}$GY
ELP expression

Plasmids encoding V12, V24, and CryS96 were generously provided by the MacKay lab. ELP constructs were expressed in BL21 (DE3) *E. coli*, using methods similar to those previously published. Competent BL21 cells were transformed with ELP plasmid constructs using standard heat shock methods and plated on selective agar. Individual colonies were chosen for expression and used to inoculate 5 mL of LB in 50 mL conical tubes. This starter culture was grown in an incubator/shaker at 300 rpm and 37° C. for 18 h; the cells were then pelleted by centrifugation at 6,000×g for 10 min, resuspended in TBPV (Terrific Broth supplemented with 10 mM proline and 100 mM valine), and transferred to a total of 333 mL TBPV in a 2 L flask. Primary cultures were shaken at 300 rpm and 37° C.; induced cultures had 2 mM IPTG added to the TBPV in the primary cultures. After 24 h, cells were collected by centrifugation at 6,000×g for 15 min and excess media was decanted. Cell pellets were flash frozen and stored at −80° C. until further work-up.

Cell Lysis
Conventional Physical and Chemical Lysis

Following expression, cells were lysed using standard procedures for physical or chemical lysis. For physical lysis, cells were thoroughly resuspended in pure water (4 mL per 1 g wet pellet weight) and incubated, on ice, with lysozyme (50-500 μg/mL) for 30-60 min with periodic mixing. Then, the cell suspension was probe tip sonicated, on ice, with a ⅛" microtip and a 30% duty cycle for 15 min. One of two lysis buffers were used for chemical lysis: homemade buffered urea or commercial B-PER (Thermo Fisher Scientific). For the urea method, cells were thoroughly resuspended in lysis buffer (8 M urea, 100 mM $NaH_2PO_4$, 10 mM Tris, pH 8.0; 4 mL per 1 g wet pellet weight) and incubated at 20° C. for 1 h on a shaker. The B-PER method was followed according to manufacturer instructions, resuspending the cell pellet with lysozyme (0.1 mg/mL) in 4 mL B-PER per 1 g wet pellet weight and a 15 min incubation with shaking at 20° C. After lysis, regardless of method, insoluble debris was pelleted by centrifugation at 15,000×g for 15 min and decanted to obtain clarified lysate for use in subsequent steps.

Combined Lysis and Purification by Organic Solvent Extraction

For the combined lysis and purification approach, cell pellets were thoroughly resuspended in the organic solvent extractant of choice, similarly to the methods previously described. The rest of the lysis and purification procedure was patterned after the organic extraction purification method for cell lysates and is described in the section on organic extraction from whole cells.

ELP Purification
ITC

Target ELP were subjected to one or more rounds of ITC using the general method published by Meyer, et al.

Organic Solvent Extraction from Cell Lysates

ELP were purified at 20° C. using an organic extraction similar to that described for GFP. For all small scale screening, 100 μL of clarified lysate was used for extraction using the following general steps at 20° C. Initially, a non-optimized extraction method (FIG. 1A) was performed. In a 1.5 mL microcentrifuge tube, 60 μL of 5 M NaCl and 500 μL of a saturated $(NH_4)_2SO_4$ solution were combined as an aqueous salt solution, followed by 400 μL of the organic extractant laid over the top. Clarified lysate (100 μL) was then added to the organic phase and the mixture was immediately vortexed for 5-10 s prior to centrifugation at 8,000×g for 5 min. After centrifugation, the upper organic phase containing the target protein was selectively recovered by pipetting, taking care to avoid the aqueous subphase and precipitated interphase. A similar procedure was followed when separating the process into two steps by first extracting the lysate with only organic solvent, adding the aqueous salt solutions to the recovered organic phase, and again recovering the upper organic phase after centrifugation (FIG. 1B). Larger scale extractions were performed using the same relative volumes.

Organic Extraction from Whole Cells

The process for extraction directly from whole cells (pelleted cells with the supernatant removed) is patterned after that used for extraction from cell lysates. For this direct extraction procedure, target protein was extracted at 20° C. with 4 mL of organic extraction solvent per 1 g wet pellet. The samples were then thoroughly vortexed, bath sonicated for 1-5 min, and periodically mixed for 15-60 min. In cases including added salts in the process, aqueous salts were added after the cell pellet was resuspended in organic solvent. After the incubation period, insoluble cellular debris was pelleted at 15,000×g for 15 min and the extraction solvent was recovered.

Target Protein Recovery Methods

Back-Extraction from Organic Solvent

Protein samples in organic solvent were concentrated and recovered in water by back-extracting at 20° C. in a centrifuge tube. Typically, a small amount of water (10-50% of the volume of lysate used in the initial extraction) was first added to the protein solution and mixed thoroughly. Then, 2-5 volumes of anti-solvent (usually ethyl acetate or diethyl ether) was added to the solution until it became cloudy before brief centrifugation to facilitate phase separation. In most cases, the lower aqueous phase was approximately equivalent to the volume of water initially added. Finally, the upper organic phase was removed, leaving the remaining aqueous subphase that contained the target protein.

Alternative Recovery Methods

A variety of evaporative strategies were used to assess the efficiency of ELP recovery. For passive evaporation, samples (typically in organic solvent) were either placed on an orbital shaker in a 37° C. environment or placed under a focused stream of air or N2 at ambient temperature until dry. Alternative methods employed rotary evaporation or lyophilization (~100 mTorr). Lyophilized samples were first back-extracted into water, then flash frozen without the addition of cryoprotectants, and loaded into a lyophilizer and processed until all the water was removed. Regardless of the recovery method used, samples were re-dissolved in water prior to analysis.

Electrophoretic Analysis

SDS-PAGE

Target proteins were separated via SDS-PAGE to identify purification efficiency and provide initial confirmation of protein identity by molecular weight, compared to a molecular weight ladder Bluestain 2 (Gold Bio). Proteins were electrophoresed through a 15% resolving gel with a 5% stacking gel in a Tris-glycine buffer system. Samples were prepared using a 2× loading solution consisting of stacking gel buffer, glycerol, SDS, BME, urea, and bromophenol blue and incubated for 5 min at 95° C.; electrophoresis was carried out at 180 V for 45-60 min at 20° C.

Following electrophoresis, proteins were stained with Coomassie Brilliant Blue G-250 using standard procedures. Briefly, for rapid Coomassie staining, gels were rinsed with water and soaked in a mixture of 40% MeOH and 10% HOAc for one min. Next, the gels were immersed in Coomassie stain solution (0.25% w/v Coomassie Brilliant Blue G-250, 40% MeOH, 10% HOAc), microwaved for ~25 sec in the stain solution, and incubated for 10 min with gentle rocking. Gels were de-stained in deionized water or de-stain solution (40% MeOH, 10% HOAc) until sufficient contrast was apparent. Finally, gels were typically imaged using a BioRad Chemidoc Touch imaging system.

Agarose Gel Electrophoresis

Agarose gel electrophoresis was used to identify the presence of contaminating nucleic acids that were not removed in the various protein purification methods. In brief, 0.5% agarose gels were cast in TBE buffer (pH 8.7) with a 1:10,000 dilution of nucleic acid detection reagent GelRed (Biotium). Samples were prepared with a 5× sample loading buffer containing TBE and glycerol; electrophoresis was conducted at 20° C. for 45 min at 80 V. After electrophoresis, gels were imaged with a BioRad Chemidoc Touch imaging system.

Additionally, agarose gel electrophoresis was used to separate and analyze proteins in cell lysates and extracts based on differing isoelectric points. Briefly, samples were prepared in 5× loading solution consisting of glycerol in TBE buffer and loaded in 1% agarose gels cast in TBE buffer (pH 8.7). Electrophoresis was conducted at 20° C. for 1 h at 80 V. Prior to Coomassie staining, gels were fixed in 25% IPA and 10% HOAc with gentle rocking for 1 h. Then, the gels were soaked in Coomassie stain solution (0.06% w/v Coomassie Brilliant Blue R-250 and 10% HOAc) until dark bands were visible; typically, staining took up to 4 h. Finally, gels were imaged in a BioRad Chemidoc Touch imager.

Alcohol Dehydrogenase Assay

Chaperone activity was measured using the alcohol dehydrogenase (ADH) aggregation assay. The kinetics of aggregation were monitored at 360 nm using a spectrophotometer equipped with a temperature controlled plate holder, Synergy Neo (Biotek). Aggregation of ADH (100 µg/300 µL) was monitored at 48° C. for 2 h. Addition of CryS96 fusion protein was used to reduce the total ADH aggregation in the samples based on chaperone activity.

Lipopolysaccharide Analysis

Analysis of lipopolysaccharide (LPS) content in the extracted protein samples was performed using a method described by Zhu and colleagues. Briefly, SDS-PAGE analysis was performed as previously described and the gels rinsed with water for 1 min. Then, the gels were oxidized in 100 mL of an $HIO_4$ solution (30% EtOH, 10% HOAc, 0.7% $HIO_4$) for 10 min before rinsing for 5 min twice in $H_2O$. Silver stain solution (0.2% $AgNO_3$) was then used to develop the gels for 5-8 min or until bands were apparent. The staining was stopped using a 10% HOAc solution. Commercial lipopolysaccharide (LPS) was serially diluted and used as a standard for visualization when comparing with extracted samples.

Copper Staining SDS-PAGE Gels

For samples requiring copper staining for detection, the following procedure was used after electrophoresis. Gels were rinsed in deionized water for 45 sec, stained with 10% $CuCl_2$ (w/v) for 5 min with gentle shaking, and minimally rinsed again with water. Finally, gels were imaged using a BioRad Chemidoc Touch imaging system.

EXAMPLES

Example 1. Screening ELP Extractability from Cell Lysates

Although relatively few examples exist for hydrophobic protein extraction from complex mixtures, the work conducted with GFP and TEL provided a starting point for the feasibility study of ELP extraction. GFP and TEL are both highly water-soluble and hydrophobic, like ELP, and this physicochemical similarity is critical for proteins intended for organic solvent extraction. Two common metrics for quantifying protein hydrophobicity are grand average of hydropathy (GRAVY) and aliphatic index. GRAVY scores account for all amino acids in a protein (Table 1), with scores ranging from −4.5 to +4.5, where +4.5 is the most hydrophobic. Aliphatic index focuses on the impact of only a handful of amino acids (isoleucine, leucine, valine, and alanine), compared to the rest of the amino acids in each protein (Table 1). The lowest possible aliphatic index score is zero, representing a very hydrophilic protein, while very hydrophobic proteins may achieve a score that slightly exceeds 100.

Even though GFP and TEL are both regarded as quite hydrophobic proteins and extractable in organic solvent, the two differ greatly in their hydrophobicity scores (Table 1). Notably, the GRAVY metric indicates GFP as hydrophilic, while the aliphatic index indicates GFP as moderately hydrophobic and similar to TEL. Since both proteins are organic solvent extractable, we reasoned that the aliphatic index might be a better general indicator of ELP extractability since it focuses specifically on the number of hydrophobic residues. Nevertheless, other metrics may prove useful for ELP, especially due to their inherently repetitive sequence, where the only variability typically arises in the guest residue or within the fusion protein domain (if present).

Even though TEL is relatively large and moderately hydrophobic, it shares a common sequence component with many ELP designs. The successful extraction of TEL led us to believe that organic solvent extraction could be a highly effective alternative purification for accessing the difficult to purify categories of ELP, especially since lower molecular weight polymers are generally more soluble than their higher molecular weight counterparts. Because TEL is known to contain patches of lysine, we anticipated that ELP containing hydrophilic guest residues or fusion peptides may also be extractable. Additionally, since organic extraction favors more hydrophobic molecules, we anticipated that more hydrophobic constructs would be most amenable to purification by organic solvent extraction.

Figure 1:
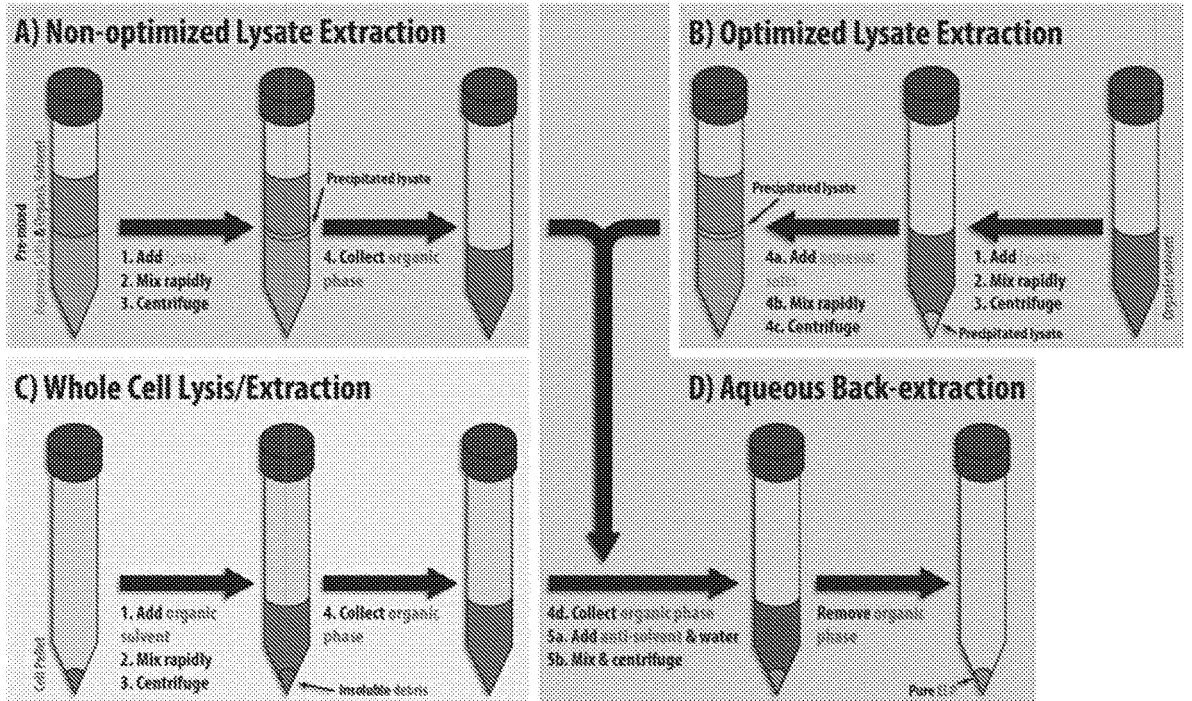
FIG. 1. Procedures for (A) non-optimized and (B) optimized lysate extraction, (C) whole cell lysis/extraction, and (D) aqueous back-extraction.

Our strategy for purifying ELP by organic solvent extraction is depicted in FIG. 1 with the original non-optimized method inspired by the procedure for GFP extraction. When the lysate is introduced into the vessel containing a salt-saturated lower aqueous phase and an organic upper phase, the dissolved proteins are either organic soluble and remain in the upper phase or become precipitated by the salts and/or organic solvent. Centrifugation expedites the

TABLE 1

Properties of Selected ELP and other Hydrophobic Proteins

| Construct ID | Class | MW (kDa)$^a$ | PI$^a$ | GRAVY$^b$ | Aliphatic Index$^c$ |
|---|---|---|---|---|---|
| GFP$^d$ | — | 27.8 | 6.30 | −0.681 | 71.6 |
| TEL$^e$ | Multiblock | 61.4 | 10.6 | 0.691 | 90.7 |
| V12 | Monoblock | 5.10 | 5.49 | 1.16 | 114 |
| V24 | Monoblock | 10.0 | 5.49 | 1.18 | 115 |
| S12-K$_4$-S12 | Triblock | 12.1 | 10.2 | −0.149 | 47.7 |
| V12-K$_4$-V12 | Triiblock | 12.4 | 10.2 | 0.673 | 95.3 |
| V24-K$_4$-V24 | Triiblock | 22.2 | 10.2 | 0.911 | 104 |
| CryS96 | Monoblock-fusion | 40.8 | 6.76 | 0.158 | 58.6 |

$^a$Molecular weight and isoelectric point were calculated based on the sequence, excluding the methionine start codon.[46]
$^b$Calculated using the expression: GRAVY = Sum of all hydropathy values ÷ Number of amino acids
$^c$Calculated using the expression: Aliphatic Index = X(Ala) + 2.9X(Val) + 3.9[X(Ile) + X(Leu)].
$^d$Based on the sequence of GFPuv-his$_8$.
$^e$TEL represents the main chain of human elastin, excluding the 26 amino acid signaling peptide.

eventual three phase partitioning, where insoluble material mostly settles between the two layers, forming a solid interphase, and the extracted proteins are easily recovered from the upper organic extractant layer.

To establish a baseline for the feasibility of ELP purification by organic extraction, we chose six ELP constructs varying in molecular weight, hydrophobicity (aliphatic index), and presence of a non-ELP element as a fusion sequence (FIG. 1, sequences appear in Sequence listings). V12 and V24 were selected because their low molecular weight places them near the lower limit of what can be reasonably purified by ITC due to their expected high $T_t$ values. Three novel triblock ELP constructs (S12-K$_4$-S12, V12-K$_4$-V12, and V24-K$_4$-V24) were also designed with two ELP blocks flanking an internal polar water-solubilizing domain containing four lysines that are in the molecular weight and hydrophobicity range that could produce lower $T_t$ values. CryS96, an ELP fusion with the αB-crystallin peptide, was chosen as a representative high molecular weight ELP fusion with a hydrophilicity similar to TEL. CryS96 has been previously purified by ITC and characterized Mackay and coworkers. Since the crystallin domain has chaperone activity, it further serves as a basis to judge whether protein activity is retained after organic solvent extraction.

Because TEL is known to be extractable in a mixed solvent system of propanol and butanol, we selected seven organic solvents of varying polarity for extraction efficiency screening. Each solvent was tested on its own and in a 1:1 (v:v) combination with the other solvents, resulting in the evaluation of 28 extractants (Table). These extractants were then used to extract each of the three ELP containing solubilizing domains from clarified lysates, using the simplified extraction procedure (Table 2). The recovered organic extract was dried by evaporation as previously for TEL, reconstituted in water equal to the original lysate volume, and analyzed by SDS-PAGE.

TABLE 2

Organic Solvent Extractants Screened for ELP Isolation.†‡

| ID | Solvent 1 | Solvent 2 |
|---|---|---|
| A | IPA | — |
| AB | IPA | nBuOH |
| AC | IPA | EtOAc |
| AD | IPA | EtOH |
| AE | IPA | MeOH |
| AF | IPA | Ace |
| AG | IPA | ACN |
| B | nBuOH | — |
| BC | nBuOH | EtOAc |
| BD | nBuOH | EtOH |
| BE | nBuOH | MeOH |
| BF | nBuOH | Ace |
| BG | nBuOH | ACN |
| C | EtOAc | — |
| CD | EtOAc | EtOH |
| CE | EtOAc | MeOH |
| CF | EtOAc | Ace |
| CG | EtOAc | ACN |
| D | EtOH | — |
| DE | EtOH | MeOH |
| DF | EtOH | Ace |
| DG | EtOH | ACN |
| E | MeOH | — |
| EF | MeOH | Ace |
| EG | MeOH | ACN |
| F | Ace | — |
| FG | Ace | ACN |
| G | ACN | — |

†All two-solvent extractant blends were mixed at a 1:1 (v/v) ratio.
‡Solvents are arranged by increasing polarity index, where A is least polar and G is most polar.

Figure 2:
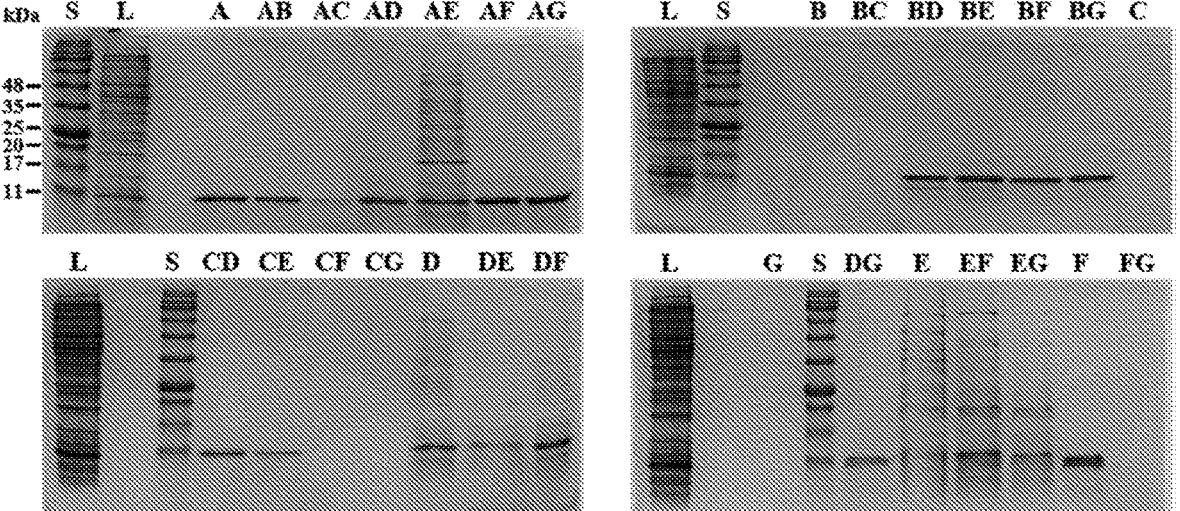
FIG. 2. SDS-PAGE analysis of V12-$K_4$-V12 extraction screen using organic extractants listed in Table 2. S=protein MW standards, L=clarified lysate.
Figure 10:
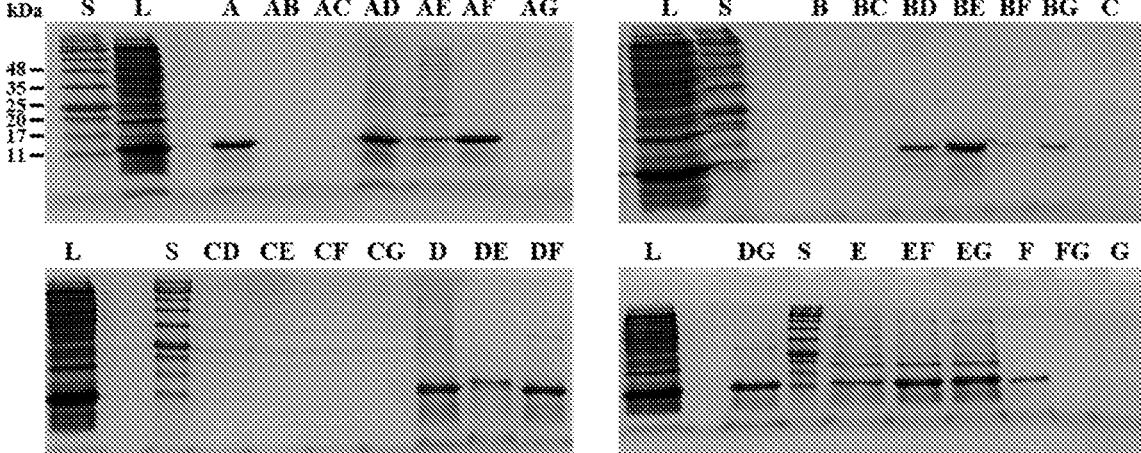
FIG. 10. SDS-PAGE analysis of S12-K$_4$-S12 extraction screen. S=protein MW standards, L=clarified lysate. Extractants used are listed in Table 2.

Extraction screens of V12-K$_4$-V12 (FIG. 2), S12-K$_4$-S12 (FIG. 10), and V24-K$_4$-V24 (FIG. 11) show successful extractions of each construct with a variety of different organic solvent extractants. The most prominent band in each lysate and extracted sample corresponds well to the expected target molecular weight for each ELP construct, based on the understanding that ELP migration is known to deviate by up to 20% from the calculated molecular weight. Notably, extraction efficiency was not universal for a given extractant across all three ELP.

ELP enrichment and recovery were highly variable for the different ELP-extractant combinations. The target ELP was enriched with 20 of the 28 combinations for V12-$K_4$-V12, while extraction of V24-$K_4$-V24 and S12-$K_4$-S12 was more selective. The general contaminant profile for a given extractant was similar and unaffected by the ELP of interest. Blends containing nBuOH and EtOAc were extremely selective for ELP, whereas MeOH and its blends were more promiscuous. Of the 28 extractants, only a few exhibited a good balance between yield and purity for all ELP, with nBuOH:EtOH standing out as the best compromise with respect to purity and yield.

Figure 12:
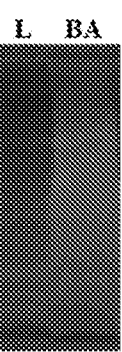
FIG. 12. SDS-PAGE analysis of V24 extraction from lysate, visualized by copper staining. L=clarified lysate; BA=1:1 nBuOH:IPA.

Initial screens with smaller constructs such as V24 using 1:1 blends of nBuOH:IPA, nBuOH:Ace, and nBuOH:ACN were explored since these worked well for the V12-$K_4$-V12 construct of similar molecular weight. Although detection of this very low molecular weight V24 protein is difficult using standard stains, extraction with nBuOH:IPA (FIG. 12) appeared successful. More rigorous analysis would be needed to fully assess V24 and V12 extraction efficiency, particularly since the latter was even more challenging to resolve and identify via SDS-PAGE (data not shown).

From the initial extraction screens, we hoped to discern extractability relationships between ELP hydrophobicity and solvent polarity. We anticipated that S12-$K_4$-S12 would be most readily extracted by more polar solvents, like MeOH, while the more hydrophobic V12-$K_4$-V12 and V24-$K_4$-V24 constructs would be more efficiently extracted in less polar solvents, like IPA. Unfortunately, we were unable to discern any clear trends relating ELP and solvent properties, even when considering additional solvent properties and multiple metrics for ranking solvent polarity (Table 3). A larger and more diverse ELP library may be required to potentially uncover any existing relationships between ELP extractability and solvent polarity.

TABLE 3

Comparison of ELP Recovery Methods.

| Method | Benefits | Limitations |
|---|---|---|
| ITC | High recovery potential | Limited to ELP with convenient $T_t$; requires aqueous solution |
| Back-extraction | High efficiency; solvent exchange to aqueous solution; target never dried | Care must be taken to avoid target precipitation; process may require optimization |
| ACN precipitation | High throughput/scalable, additional small molecule removal rapidly | Precipitation may lead to loss of protein structure/function |
| Passive evaporation | High efficiency | Relatively slow process, depending on solvent; may lose structure/function upon drying |
| Rotary evaporation | Highly scalable for large volumes; high efficiency | May lose structure/function upon drying; may be slow, depending on solvent |
| Vacuum drying | High throughput; high efficiency | Limited utility with highly volatile solvents; may lose structure/function upon drying |

TABLE 3-continued

Comparison of ELP Recovery Methods.

| Method | Benefits | Limitations |
|---|---|---|
| Speed vac | High throughput; high efficiency | May lose structure/function upon drying |
| Lyophilization | High throughput; high efficiency | Slow; requires transition to aqueous solution; may lose structure/function without the use of cryoprotectants |

Example 2. Optimizing Extraction from Lysates

After identifying the best extractants from the initial screen and subsequent optimization, we wanted to further optimize the extraction process to maximize yield and purity. The initial screens used a single lysate:extractant ratio (1:4 v/v) which was effective, but potentially sub-optimal for achieving the highest yield with minimal solvent. Additionally, even though aqueous NaCl and (NH$_4$)$_2$SO$_4$ were necessary in the published method for GFP extraction, we anticipated that they may be unnecessary additions for process improvement, since many of the most effective extractant blends already phase separated from the aqueous medium and precipitated non-target proteins on their own. Excluding these salts would simplify the process and reduce additional downstream processing for their removal.

Figure 14:
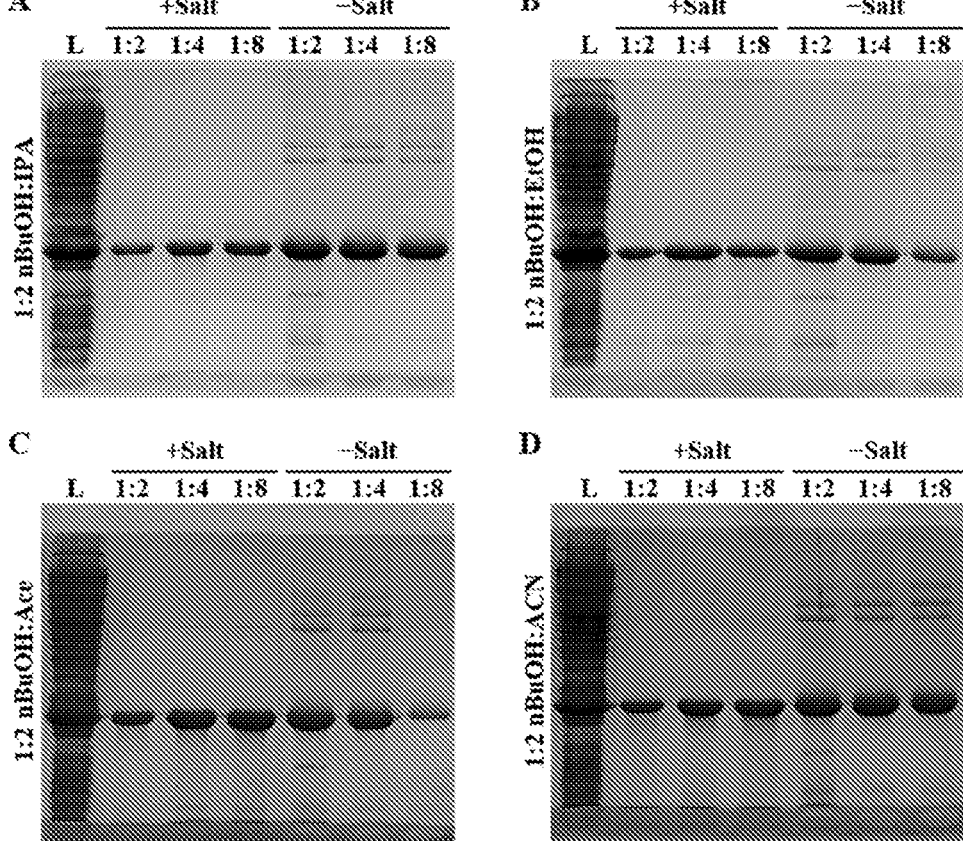
FIG. 14. SDS-PAGE analysis showing extraction optimization of V24-K$_4$-V24 with varied lysate:extractant ratios and salt effects. L=clarified lysate.

We interrogated the effects of varying lysate:extractant ratios and the absence of added salts on extraction efficiency using the preferred extractant blends for V24-$K_4$-V24 and analyzed the extracts by SDS-PAGE (FIG. 14). In the absence of salts, the original 1:4 lysate:extractant ratio provided target enrichment with all extractants, although the extracts were less pure than previously seen with salt-containing aqueous phases. Lower lysate:extractant ratios (1:2) were equally effective, indicating that an even lower extractant volume might be used without a loss in recovery. It is important to note; however, that the ideal lysate:extractant ratio may vary as a function of construct type, extractant composition, and lysate concentration. When including NaCl and (NH$_4$)$_2$SO$_4$, there appeared to be no risk of increasing the lysate:extractant ratio, although yield was consistently reduced at the expense of increased purity. Some extractant blends, namely 1:2 nBuOH:EtOH and 1:2 nBuOH:Ace (FIGS. 14 B & C), did show evidence that too much extractant may inhibit, rather than boost, target and contaminant protein extractability in the absence of added salts. Consequently, caution should be taken when choosing the appropriate lysate:extractant ratio.

Figure 15:
FIG. 15. SDS-PAGE analysis of lead extractant blend ratio optimization for V24-K$_4$-V24. Blend ratios (v/v) are as indicated for each solvent combination.
Figure 15:
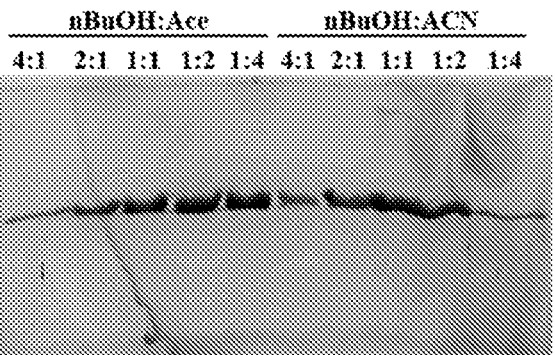

Having established the ideal lysate:extractant ratio and a need for NaCl and (NH$_4$)$_2$SO$_4$ salts to reach high purity, we sought to further improve the extraction efficiency of V24-$K_4$-V24 by screening the blend ratios of the leading extractant blends across the range of 4:1, 2:1, 1:1, 1:2, and 1:4 (v/v). As shown in FIG. 15, each of the four extractant blends with nBuOH showed a similar trend and resulted in extremely pure ELP. As expected, since pure nBuOH was ineffective, all the 4:1 ratios of nBuOH with the other solvents significantly reduced the amount of ELP extracted. Reducing the nBuOH content increased ELP recovery, but too little butanol again reduced efficiency, as was especially visible with nBuOH:ACN mixtures. From this data, a 1:2 ratio was identified as ideal for nBuOH blended with either IPA, EtOH, or Ace; the original 1:1 ratio was optimal for nBuOH:ACN.

Figure 3:
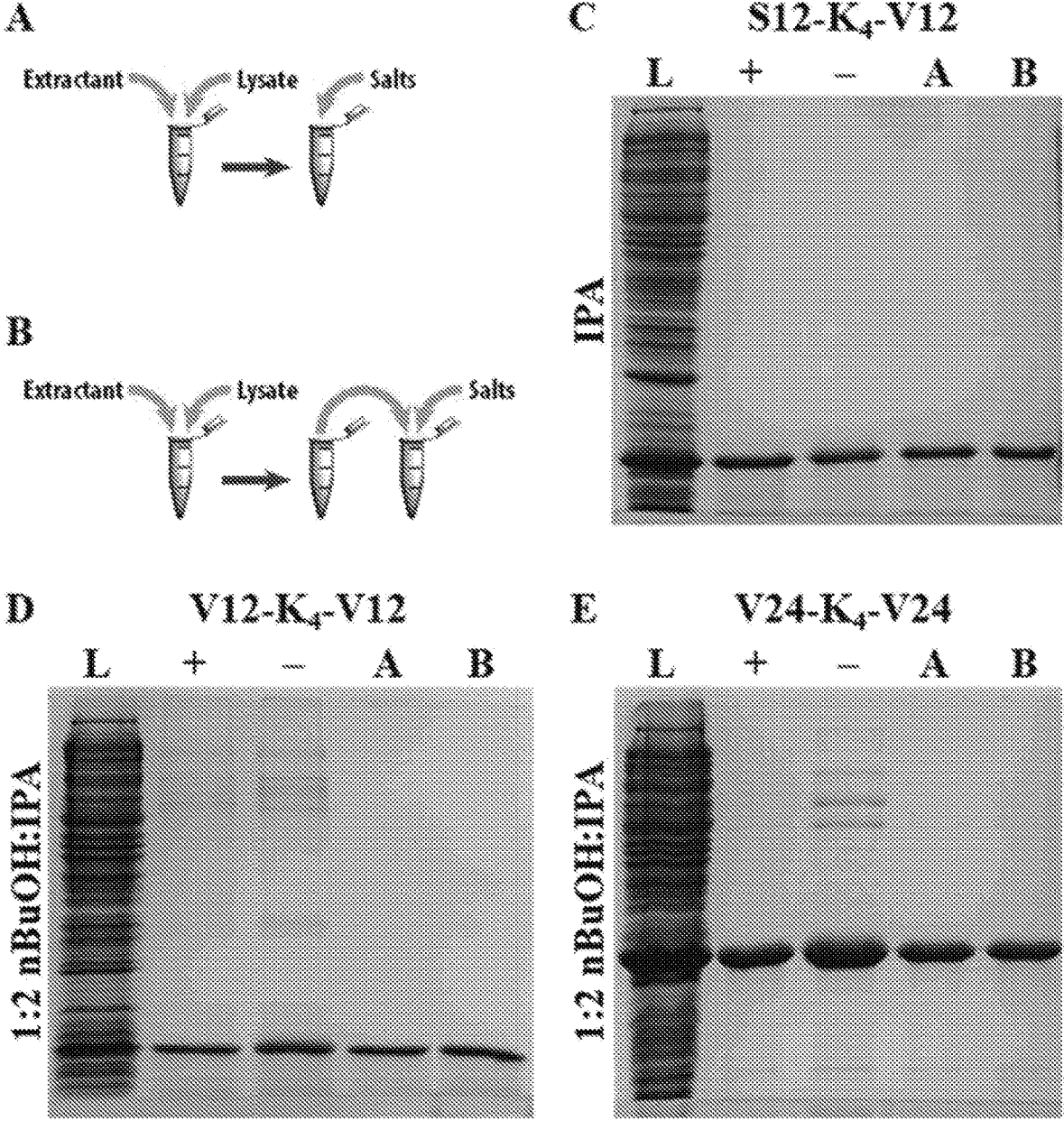
FIG. 3. SDS-PAGE analysis of ELP extractions from lysate using (A) optimized method A and (B) optimized method B for (C) S12-$K_4$-S12, (D) V12-$K_4$-V12, and (E) V24-$K_4$-V24. L=clarified lysate; "+"=non-optimized method with salt; "−"=non-optimized method without salt.

Extractions in the presence of high concentrations of NaCl and $(NH_4)_2SO_4$ have been well-studied for GFP. Since the data in FIG. 14 show greater recoveries in the absence of added salts, we hypothesized that aggressive salting out of contaminating proteins may also be non-specifically entraining the desired ELP. This phenomenon could be especially problematic at the relatively high protein concentrations present under these conditions. On the other hand, the presence of salts significantly improved sample purity and could not be completely excluded. As an alternative strategy, we chose to split the one-step method into two sequential steps (FIG. 1B) to first extract the target ELP in high yield and then remove contaminating proteins from this ELP-enriched solution in a second extraction step with added salts. Using an optimized extraction blend for each of the three triblock ELP, we investigated this optimized two step method in two different ways after performing the initial salt-free extraction and compared them to the original one step extraction (FIG. 3). Using optimized method A (FIG. 3A), we added the salt solution directly to the same tube containing pelleted debris and the extracted ELP solution supernatant. For optimized method B (FIG. 3B), we transferred only the ELP extract solution to a new tube containing the salt solution.

The extraction solvent, dictated by the ELP construct of interest, clearly plays a key role in identifying the most productive extraction method (FIG. 3). For IPA extraction of S12-K$_4$-S12 (FIG. 3C), purity and yield were completely unaffected by the extraction method used. For V12-K$_4$-V12 and V24-K$_4$-V24 (FIGS. 3C & D), the same extractant (1:2 nBuOH:IPA) generated similar patterns of sample purity. The non-optimized extraction method provided highly enriched and relatively pure ELP, while salt omission resulted in lower purity. Greater variation in extraction yield was expected based on the extraction method employed; however, this was only the case for V24-K$_4$-V24. The optimized two step methods A and B performed equivalently, while drastically improving purities to ≥95%. We infer from these findings that the protein content of the debris pelleted in the initial extraction step cannot be readily resolubilized when the salt solution is added in the second step. Thus, optimized method A in a single tube is preferred due to higher throughput and less potential sample loss because there are fewer sample transfers.

Example 3. Post-Extraction ELP Recovery

Traditionally, the main benefit of working with ELP is their unique capacity to undergo a sequence-dependent aggregation and isolation via the ITC method. This property makes the recovery of ELP from aqueous solutions very convenient compared to conventional protein isolation methods. However, there are limitations to ITC purification, such as the occurrence of ELP sequences with transition temperatures that are impractical. Due to the demonstrated solubility of ELP in various organic solvents, several alternatives are available for recovering the construct from solution (Table 3). These methods have different benefits and limitations depending on the properties of the ELP. Based on our experience, the primary challenge that may be encountered is that, in some instances, the recovered ELP does not dissolve readily in either $H_2O$ or the organic solvent it was extracted with (data not shown). Although we have not thoroughly investigated these occurrences, we have observed that rotary evaporation to dryness caused the most problems, whereas passive evaporation was nearly always successful.

Figure 4:
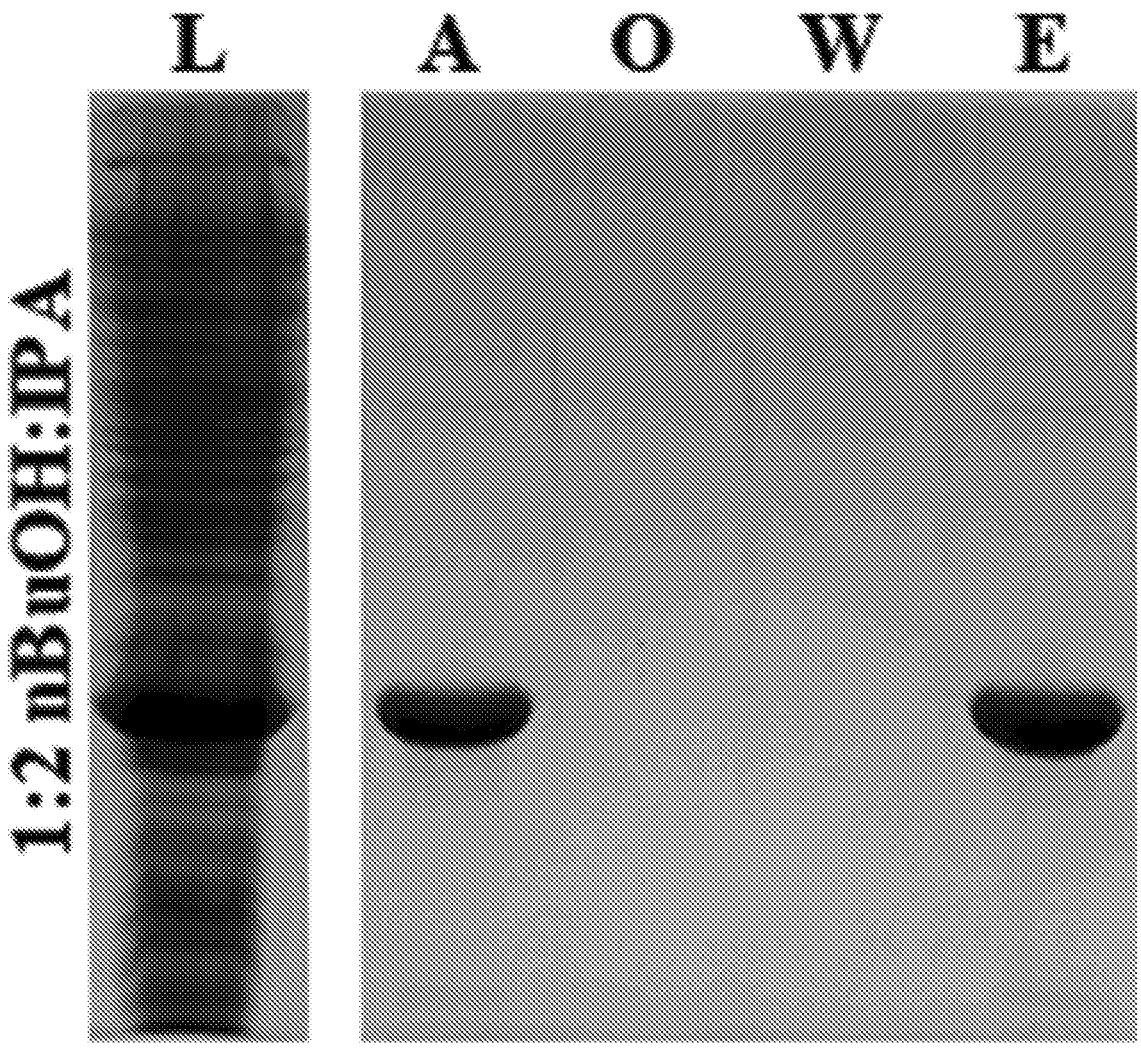
FIG. 4. SDS-PAGE analysis of V24-$K_4$-V24 back-extraction with EtOAc compared to the original organic extract. L=lysate; A=aqueous subphase after back-extraction; O=organic phase after back-extraction; W=organic wash of A; E=organic phase prior to back-extraction.

Back-extraction is a rapid and attractive alternative recovery method, since the target protein always remains in solution and re-dissolution issues are bypassed. Back-extraction from organic solvent into aqueous solution was a critical step in the optimized extraction of GFP (specifically, nBuOH was added as anti-solvent to drive GFP from ethanol and into the aqueous layer). In contrast, we found that nBuOH was often useful as an ELP extractant. Consequently, our back-extraction process (FIG. 1D) required a different anti-solvent that was miscible with the chosen extractant, immiscible with water, and does not extract the target ELP. We employed broad extractant screens to identify potential anti-solvents for our ELP constructs. Using V24-K$_4$-V24 as an example, we successfully back-extracted this ELP from 1:2 nBuOH:IPA into water by adding EtOAc as anti-solvent (FIG. 4). The rapid back-extraction process appeared to be lossless in comparison to the original extraction process, thus suggesting that this method presents an opportunity to concentrate the protein in an aqueous acceptor medium via a rapid and simple process. Additionally, subsequent washes with anti-solvent did not affect ELP recovery. Following this same approach, we also back-extracted S12-K$_4$-S12 and V12-K$_4$-V12 using EtOAc; we also had mixed success when using other anti-solvents such as diethyl ether (data not shown).

Figure 5:
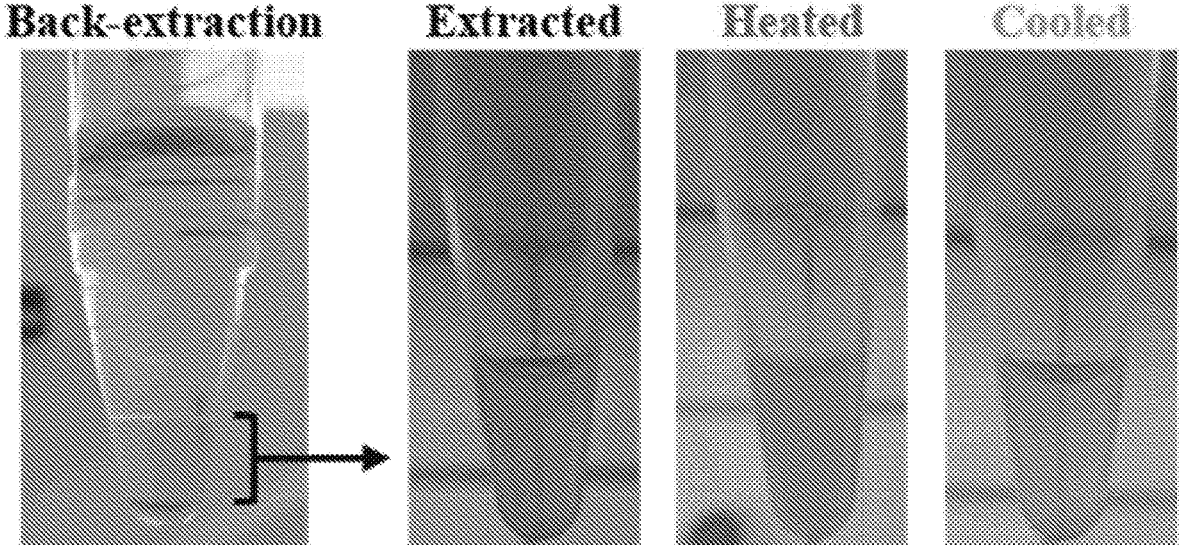
FIG. 5. Thermal transition behavior of V24-$K_4$-V24 back-extracted after extraction from whole cells with 1:2 nBuOH: IPA. The arrow indicates the aqueous sub-phase recovered for thermal transitioning.

Next, we evaluated the functional properties (e.g., $T_t$) of the back-extracted ELP by testing the temperature transition behavior of V24-K$_4$-V24 (i.e., between 35-50° C., depending on the protein and salt concentrations). After organic extraction from lysate or whole cells, drying by passive evaporation or lyophilization, and re-solubilization in water, these ELP retain their ability to reversibly transition when heated and cooled. Following back-extraction, V24-K$_4$-V24 was able transition with gentle heating (~40° C.) and re-solubilize when cooled to 20° C. (FIG. 5). This reversible thermal transitioning demonstrates that the basic ELP functional character has not been altered throughout the extraction and back-extraction processes.

Example 4. ELP Extraction from Whole Cells

Figure 13:
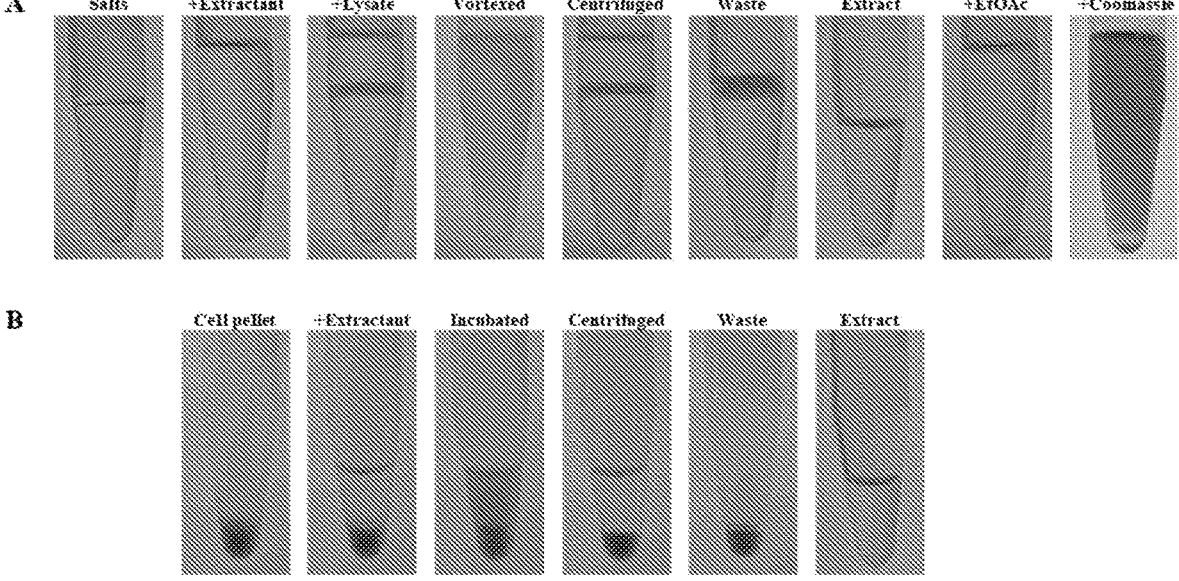
FIG. 13. Photos depicting the steps of the non-optimized extraction from cell lysate (A) and whole cells (B). Coomassie Blue was added after back-extraction to enhance visibility of the aqueous subphase.

To explore the full potential of the organic extraction method for ELP purification, we adapted the procedure for target protein extraction directly from whole cells, rather than clarified cell lysates. By combining cell lysis with ELP extraction in a single step, the overall process of recovering pure protein from cell culture would be accelerated, greener, and minimize opportunities for protein degradation during isolation. Since many of the organic extractant blends should have the propensity to disrupt bacterial cells and liberate the desired ELP in a single, combined extraction step (FIGS. 1C & 13B), we anticipated that this approach could provide superior lytic ability and yield compared to traditional methods and commercial reagents.

Figure 6:
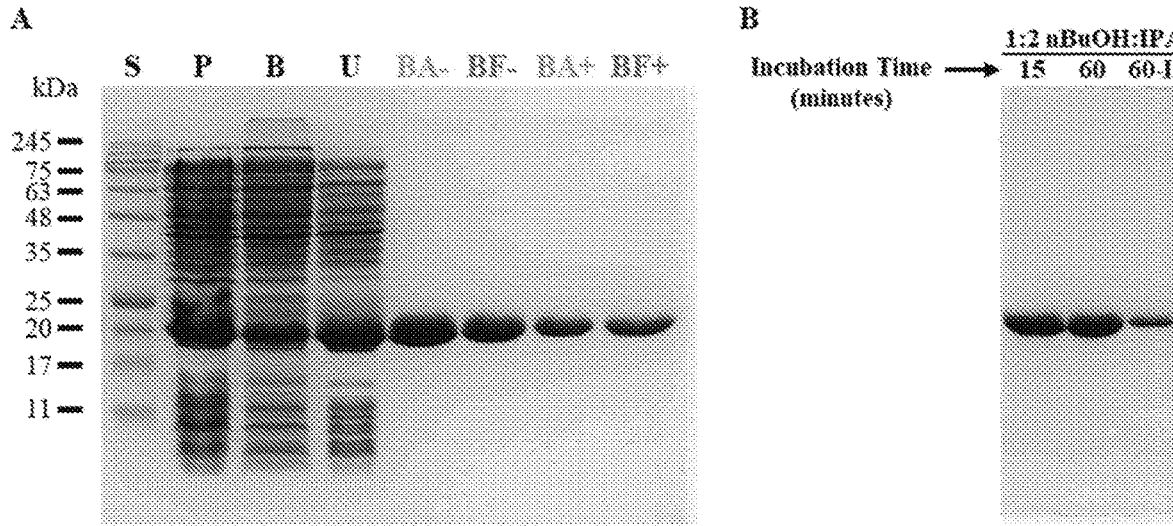
FIG. 6. (A) SDS-PAGE analysis of 60 min direct V24-$K_4$-V24 extraction from whole cells. S=MW standards, P=probe tip sonication lysate, B=B-PER lysate, U=urea lysate, BA=1:2 nBuOH:IPA, BF=1:2 nBuOH:Ace, "−"=without salt, "+"=with salts. (B) Direct extraction of V24-$K_4$-V24 after 15 and 60 min treatment with 1:2 nBuO-H:IPA. 60-I=IPTG-induced cell culture.

V24-K$_4$-V24 was selected for direct extraction of cell pellets using two of the most efficient extraction solvents for this construct, 1:2 nBuOH:IPA and 1:2 nBuOH:Ace. In both cases, extraction with a 60 min incubation was performed with and without a follow-up salting-out step. Following lysis, all samples were dried and reconstituted with water to the original volume, to allow direct comparisons of the lysis methods. The reconstituted samples were analyzed by SDS-PAGE and compared to clarified lysates generated from three standard lytic procedures: probe tip sonication, a commercial nonionic detergent solution (B-PER), and buffered urea (FIG. 6A).

Both extractant blends were highly effective in recovering a very large amount of V24-K$_4$-V24. The extracted samples were also extremely pure and showed only a single band of the expected molecular weight, indicating >95% purity. Added salts again reduced the yield as seen before with clarified lysate extraction. No detectable contaminants were observed in the absence of salt; therefore, there are no obvious benefits in going beyond simple organic solvent extraction. Since the cell pellet contains significantly less water than the corresponding cell lysate, we believe that the specific composition of the organic extractant becomes even more important than before. Thus, the extractant blend may be more selective for ELP and have less tolerance for contaminating proteins, even in the absence of additional salts.

The three traditional lysis methods looked very similar to one another, with only slight variations in ELP recovery observed. Importantly, it appeared that a greater quantity of highly pure ELP was recovered by direct organic extraction, compared to the relatively impure ELP liberated by probe tip sonication or B-PER. Based on these experiments, we conclude that traditional lysis methods may be incomplete for ELP release from cells, such that the use of these methods may reduce overall ELP yield from the start. A more quantitative analysis; however, is needed to validate these findings.

We further evaluated the extracted V24-K$_4$-V24 material by running the extracted and lysed samples on agarose gels followed by Coomassie R-250 staining (FIG. 21B). Since this ELP has a calculated isoelectric point of 10.2, while the vast majority of *E. coli* proteins have a PI below 10, we expected that the majority of proteins would migrate toward the anode, whereas the target ELP would migrate toward the cathode under the mildly basic electrophoresis conditions employed (pH 8.7). As anticipated, a large amount of protein was detected on the anode side of the well for each of the standard lysis methods, while the extracted samples did not show any protein in this area. The only protein detected in the extracted samples was found to migrate toward the cathode and showed reversible thermal transitioning behavior (FIG. 5), thus providing further evidence that the extracted protein is an ELP.

Figure 16:
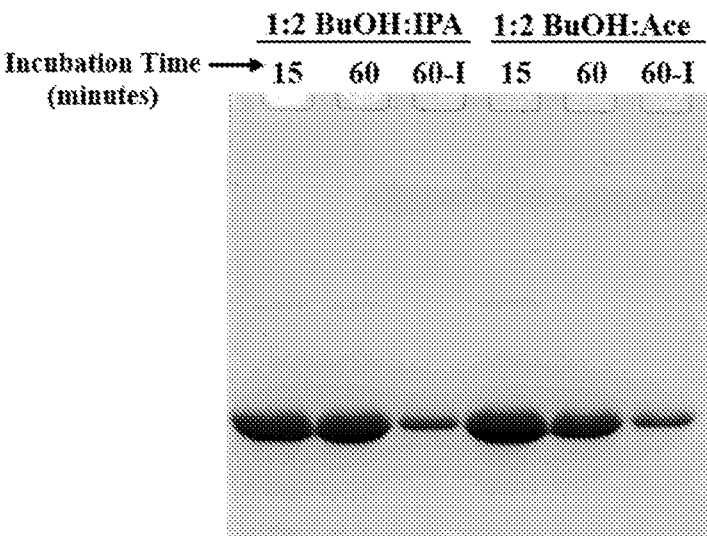
FIG. 16. SDS-PAGE analysis of 15 vs 60 min direct extraction of V24-K$_4$-V24 from whole cells. 60-I=IPTG-induced cells.

During the direct extraction process from whole cells, a very rapid visible change occurred within the first few minutes—a grainy, spongy-looking mass began to settle to the bottom of the tube. This observation, along with the expectation that the lytic and extraction processes would be very rapid, led us to shorten the extraction from 60 to 15 min to provide a more direct comparison to the B-PER procedure. Additionally, we compared the direct extraction process to cells that had been grown under IPTG induction, attempting to increase the target protein yield (FIG. 6B & FIG. 16).

As expected, the data in FIG. 5B show equivalent extraction efficiency with nBuOH:IPA at 15 min, as compared to 60 min; we expect this process could be shortened even further to just a few minutes. Extraction with nBuOH:Ace (FIG. 16) was also effective with the 15 min incubation. Although reports have indicated exceptionally high yields for ELP production under IPTG induction, the yield in our case was significantly lower for an equivalent cell mass. The reduced yield may be due to ELP entrainment within inclusion bodies. Alternatively, the stretch of lysine residues in our construct may become cytotoxic when rapidly produced. Nonetheless, extractants identified as ideal candidates from lysate screens typically also worked very well for direct extraction from whole cells. Although we encountered only few instances where lysate extractant success did not translate well to whole cells, other ELP requiring other extractants may have different results. Since the lytic effects of many solvents, especially simple alcohols, are well-known and often extremely potent in releasing cellular contents, we believe that these cases may be easily remedied without significantly altering ELP solubility by spiking in a very small amount of this solvent class.

Example 5. Extracting the ELP Fusion Protein, CryS96, from Whole Cells

Next, we investigated the extraction of an ELP fusion, specifically a relatively hydrophilic and functional ELP, CryS96 (Table 1). Since the aliphatic index of CryS96 (58.6) is most similar to S12-K$_4$-S12 (47.7), we used the results of the previous extraction screens to select a handful of extractant blends most likely to extract CryS96.

Figure 7:
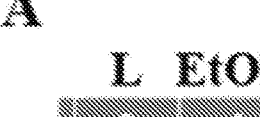
FIG. 7. SDS-PAGE analysis of (A) direct CryS96 extraction from whole cells (0.2 g) with pure ethanol. L=clarified lysate. (B) Scale-up of CryS96 extraction from whole cells.
Figure 7:
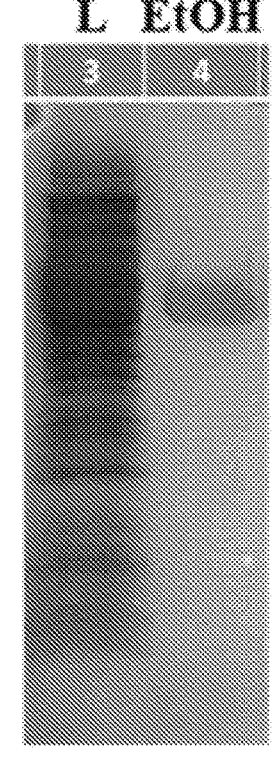
Figure 7:
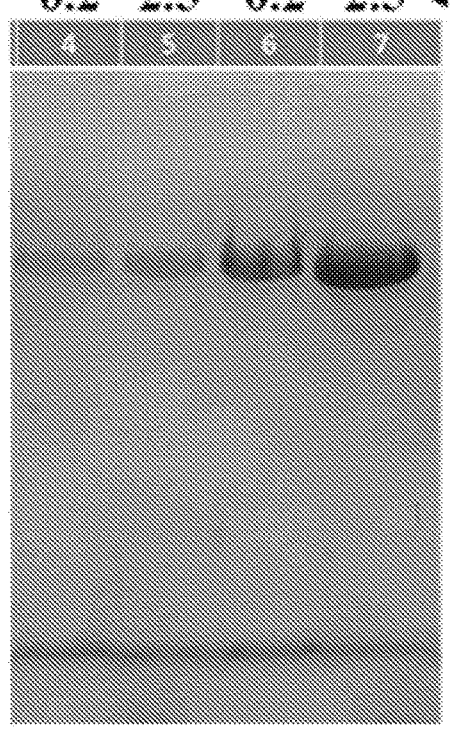

Our initial screen of CryS96 extractability was conducted using a previously purified solution of CryS96. These encouraging results led us to use the same set of solvents for extracting CryS96 directly from whole cells (FIG. 7). Of these selected extractants, pure EtOH provided the best balance of yield and purity, although other extractants, such as pure IPA (FIG. 7) and 1:1 nBuOH:EtOH (data not shown) also worked well. The T$_t$ of the EtOH extracted/EtOAc back-extracted CryS96 construct was similar to that reported previously (data not shown). This successful extraction of an ELP-fusion protein is an important milestone in showing the versatility of ELP and ELP-fusion extraction with organic solvents.

Figure 8:
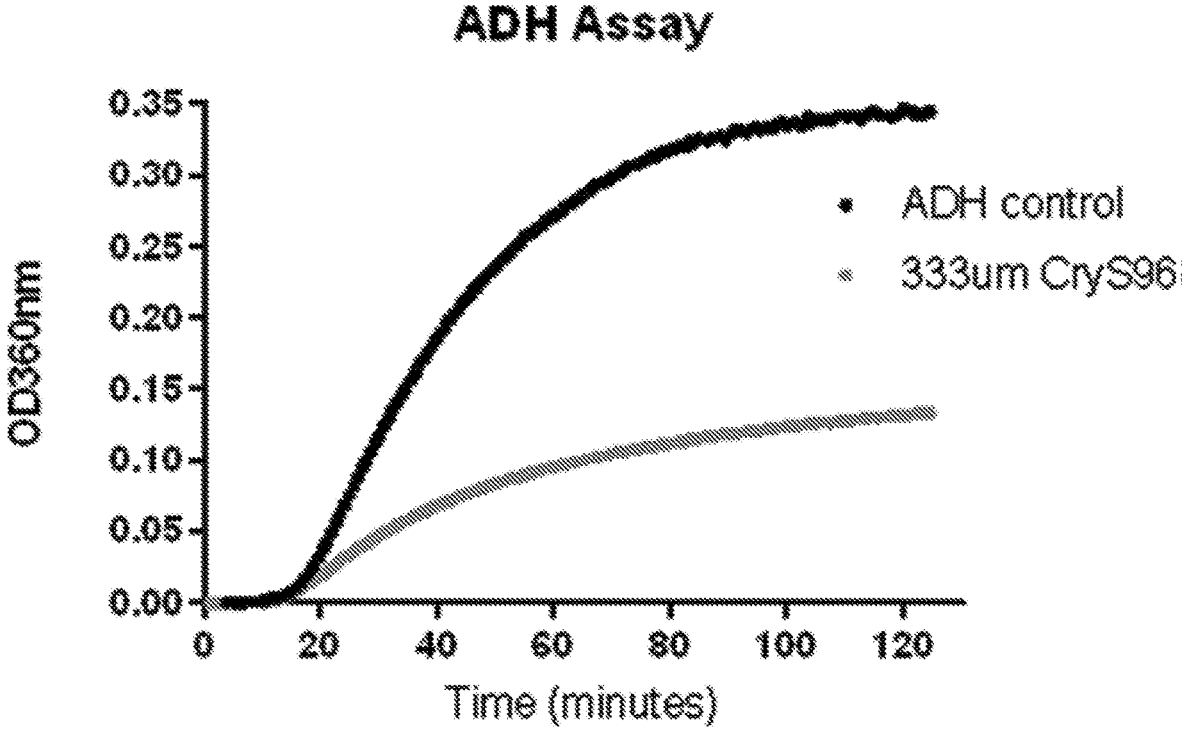
FIG. 8. Alcohol dehydrogenase activity assay. Time dependent optical density at 360 nm indicated ADH aggregation upon heating at 48° C. ADH (black, control) and ADH+Crys96 protein (gray, 333 µM CryS96) were measured every 45 s for 2 h. Data indicates mean absorbance measured at 360 nm (n=3).

Example 6. Functional Evaluation of Extracted CryS96 by Alcohol Dehydrogenase Activity Assay Previous reports of CryS96 activity from Mackay and coworkers have shown that ITC purified CryS96 is an effective chaperone protein. Using the alcohol dehydrogenase activity assay a 70% reduction in aggregation was seen with 333 μM CryS96. Based on initial screens, pure EtOH extraction followed by EtOAc back extraction generated high yield and purity (FIG. 7). Addition of 333 μM EtOH extraction-purified CryS96 led to a 61% decrease in ADH aggregation (FIG. 8), in excellent agreement with the activity reported by CryS96 that was purified by ITC. These results suggest that organic solvent extraction of ELP does not disrupt their functional activity. Further investigation of varying blends and ratios of organic extractions is warranted.

Example 7. Scale-Up of ELP Extractions from Lysates and Whole Cells

Liquid-liquid extraction (LLE) is a scalable purification technique routinely employed in industrial processes. For large-scale production of biomolecules, LLE offers numerous economic and process benefits over chromatographic purification and fits into continuous production schemes, including bioreactors. ELP purification by organic extraction must maintain a high level of efficiency, in order to be considered as a viable component of scaled-up production. As an initial step, we briefly explored extraction scalability from lysates and whole cells.

Figure 17:
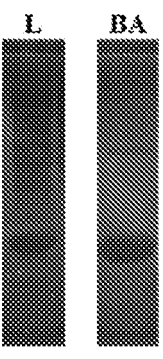
FIG. 17. SDS-PAGE analysis of scaled-up V24-K$_4$-V24 extraction from lysate (35 mL, ~8.75 g wet pellet weight), visualized by copper staining. L=clarified lysate; BA=1:2 nBuOH:IPA.

Using V24-K$_4$-V24 lysates, we performed large-scale extractions (35 mL lysate) with 1:2 nBuOH:IPA using the non-optimized method shown in FIG. 1A. Although the extraction was highly effective in recovering a large amount of ELP, some minor protein contamination remained (FIG. 17). Since our earlier experiments showed that salts could reduce protein contamination (FIG. 14), we attributed these observations to slow and/or inefficient mixing such that the contaminants were not properly salted out. We expect that the optimized extraction procedure (FIG. 3) could minimize contaminants in larger scale lysate extractions.

Figure 18:
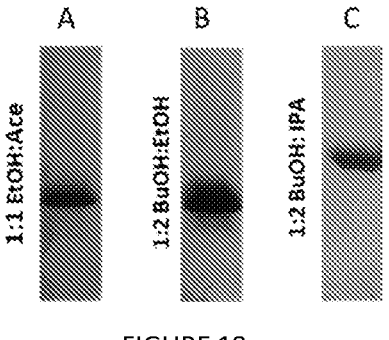
FIG. 18. SDS-PAGE analysis of scaled-up (A) S12-K$_4$-S12, (B) V12-K$_4$-V12, and (C) V24-K$_4$-V24 extractions from whole cells with extraction blend ratios (2.5 g of cell pellet).

Finally, we investigated extractions of S12-K$_4$-S12, V12-K$_4$-V12, and V24-K$_4$-V24 with 1:1 EtOH:Ace, 1:2 nBuOH: EtOH, and 1:2 nBuOH:IPA, respectively, on the 2.5 g scale using whole cells. All three ELP were successfully extracted at this scale (FIG. 18). S12-K$_4$-S12, for example, shows an equivalent yield and purity at both small (0.2 g) and large (2.5 g) scales. Similarly, whole cell extraction of CryS96 was equally efficient, regardless of scale, when extracting with IPA or EtOH (FIG. 7B). Based on these collective preliminary results for scaling extractions more than 10-fold from lysates and whole cells, we believe that organic solvent extraction is a viable, valuable, and rapid process for scalable ELP purification.

Example 8. Analysis for the Presence Co-Extracted Contaminants

Nucleic Acid Analysis

Figure 19:
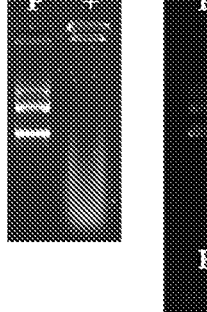
FIG. 19. Nucleic acid contamination of V24-K$_4$-V24 extraction from lysates assessed by agarose gel electrophoresis and stained with GelRed. P=plasmid DNA control; "+"=3×ITC-purified V24-K$_4$-V24. Extractants employed are listed in Table 2 of the paper.
Figure 19:
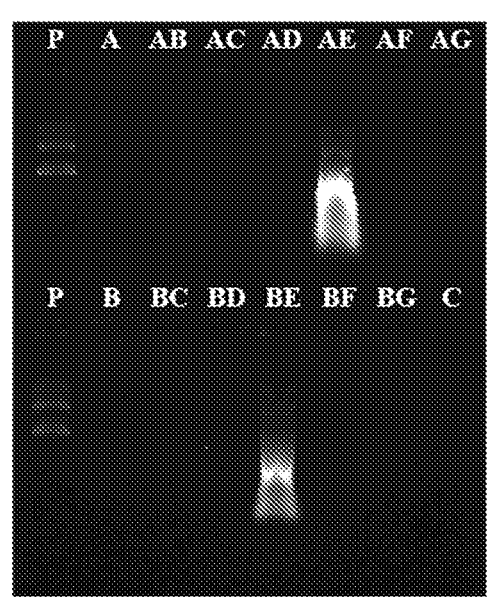
Figure 19:
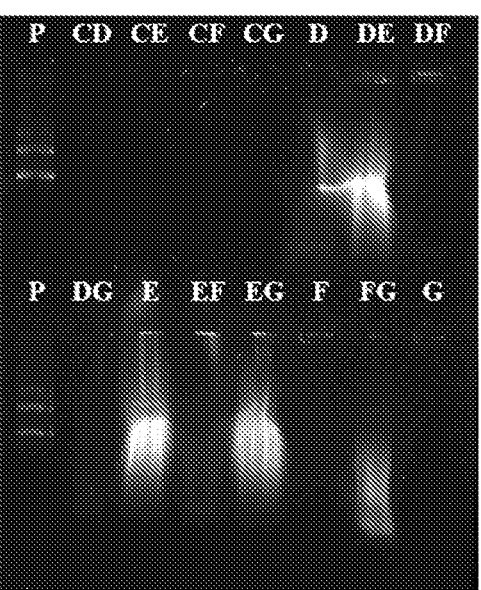

Nucleic acid contamination is a prevalent issue when ELP are purified by ITC; however, this problem was not anticipated for the organic solvent extraction procedure. Using V24-K$_4$-V24 lysate as a test case, we analyzed each of the 28 organic solvent extraction combinations via agarose gel electrophoresis using GelRed to stain for nucleic acids such as dsDNA, ssDNA, and RNA (FIG. 19). For comparison, we included a sample purified by three rounds of ITC. Notably, ITC-purified V24-K$_4$-V24 still has a considerable amount of nucleic acid contamination and would require an additional step of adding branched polyethylenimine (bPEI) to precipitate the nucleic acids. Although often effective, the additional time and resources can lead to complications and reduce the recovery of certain ELP constructs.

Figure 20:
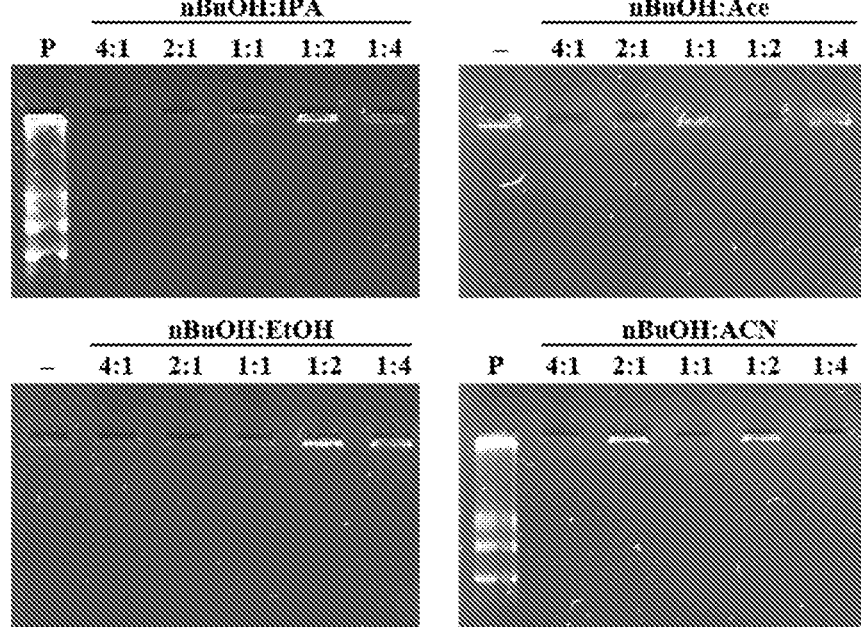
FIG. 20. Agarose gel electrophoresis assessment of nucleic acid contamination of optimized extractant blends for V24-K$_4$-V24 purification from lysates. Blend ratios (v/v) are as indicated for each solvent combination. P=plasmid DNA; "−"=empty lane.

For most organic extractants, there was no detectable nucleic acid contamination arising from the extraction process, except for extraction solvents containing MeOH and the Ace:ACN combination. The nucleic acid contaminants in the MeOH and Ace:ACN cases are likely plasmid DNA based on their comparative migration relative to control DNA. Even though a handful of samples contained contaminating nucleic acids, the most promising extractants for isolating nucleic acid-free ELP lacked MeOH and contained nBuOH, the latter serving to prevent carryover (FIG. 20).

Figure 21:
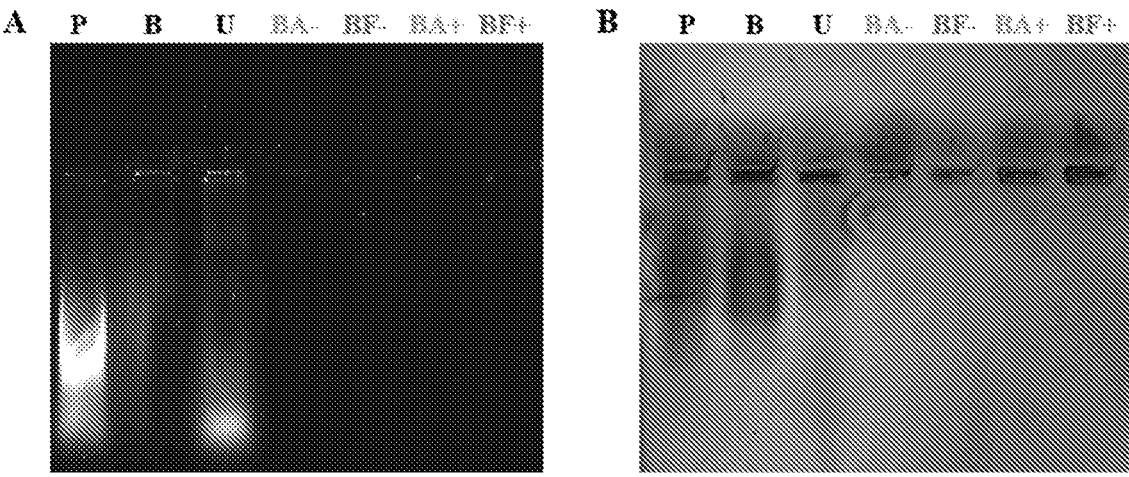
FIG. 21 Agarose gel electrophoresis of V24-K$_4$-V24 extracted directly from whole cells. (A) Nucleic acids are visualized by GelRed staining and (B) proteins by Coomassie R-250 staining. P=probe tip sonication lysate, B=B-PER lysate, U=urea lysate, BA=1:2 nBuOH:IPA, BF=1:2 nBuOH:Ace, "−"=without salt, "+"=with salts.

Having demonstrated that organic extraction from cell lysates typically excluded nucleic acid carryover, we similarly evaluated contamination when extracting directly from whole cells by subjecting 60 min extractions and lyses of V24-K$_4$-V24 to agarose gel electrophoresis (FIG. 21). All three standard lysis methods showed a considerable amount of nucleic acid contamination, as anticipated. Regardless of the extractant or salt composition used; however, no nucleic acids were detectable using the direct extraction method from whole cells. Based on these results, we expect that other extractant blends will also exclude nucleic acid contamination.

Lipopolysaccharide Analysis

Figure 22:
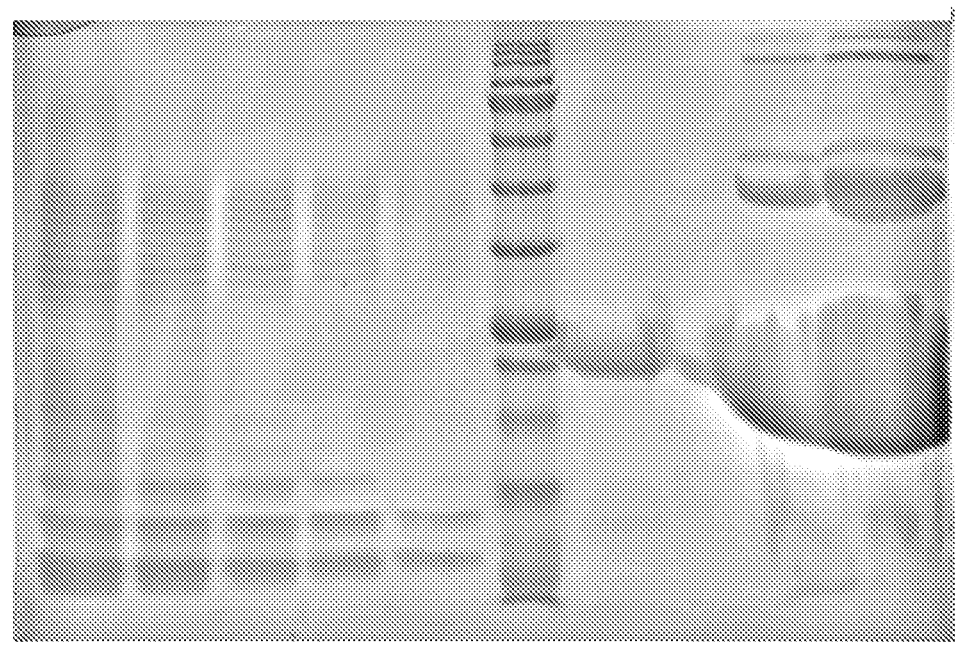
FIG. 22 SDS-PAGE analysis of LPS content in V24-K$_4$-V24 extracted from lysates with 1:2 nBuOH:EtOH. Lanes 1-5 are a serial dilution of commercial LPS from 500 ng-31.25 ng. Lane 7, 9, and 10 contain 5, 30, and 50 µg of V12-K$_4$-V12 extract, respectively.
Figure 23:
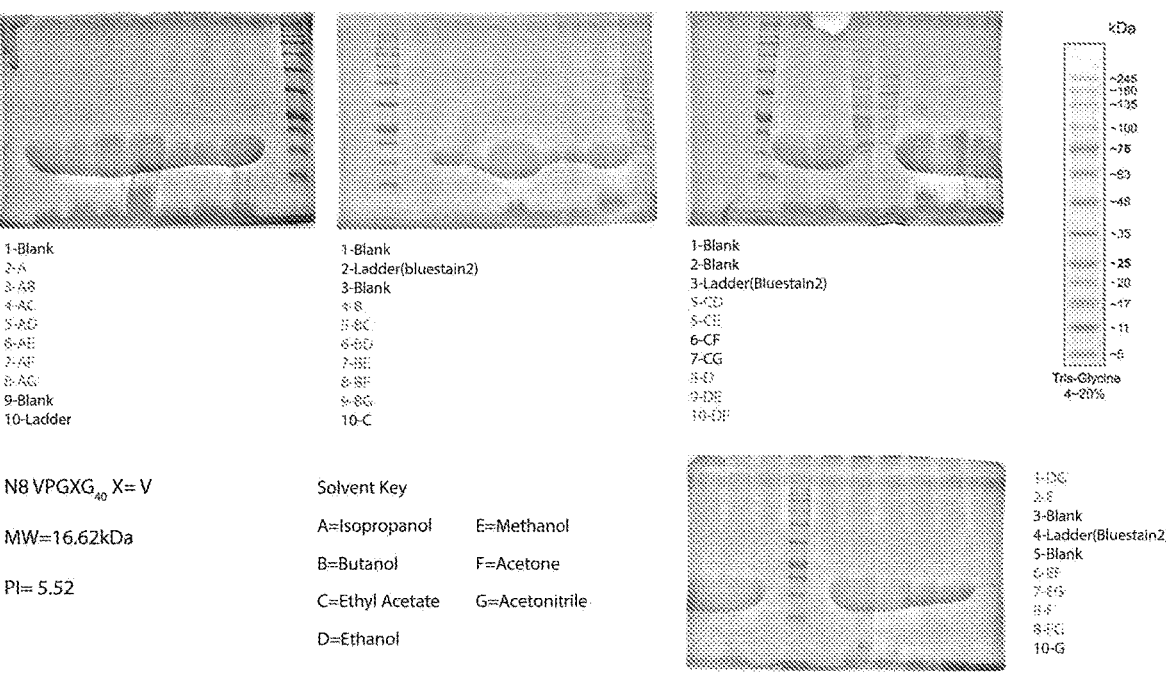
FIG. 23. Extraction Screen of Acidic N8 Elastin Like Polypeptide. Glycerol stocks were used to make an overnight starter culture of *E. coli*. 2 liter flasks containing 333 mL of terrific broth were inoculated and grown for 24 hours. 50 mL falcon tubes were filled with equal volume and were spun at 6000×g for 20 minutes to pellet bacterial cells and frozen until used. 28 conditions of pure and mixed solvents were used to extract protein. Briefly the pellet was weighed and extracted with 4 times (w/v) of the desired organic solvent. Samples were vortexed for 30 seconds and spun at 8000×g for 15 minutes. The supernatants were decanted into a new tube and evaporated under air. Samples were then resuspended and SDS-PAGE was run to determine protein purity. Gels were rinsed with water for 15 minutes 3 times and stained in colloidal Coomassie overnight.
Figure 24:
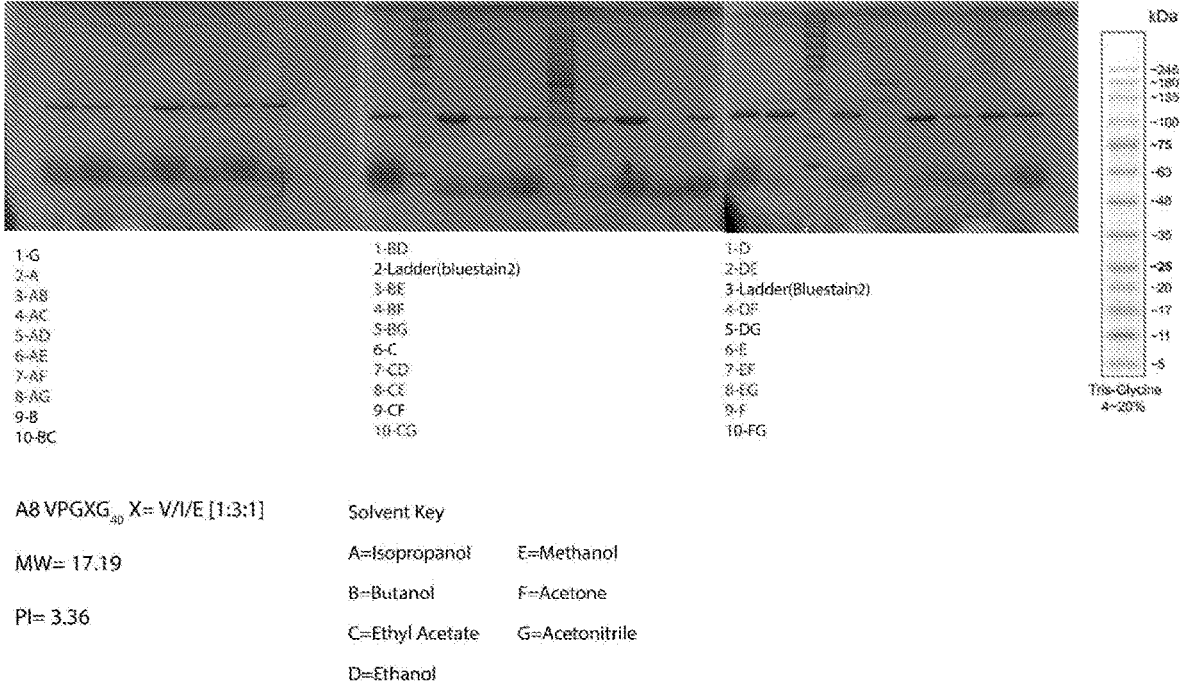
FIG. 24. Extraction Screen of Acidic A8 Elastin Like Polypeptide. Glycerol stocks were used to make an overnight starter culture of *E. coli*. 2 liter flasks containing 333 mL of terrific broth were inoculated and grown for 24 hours. 50 mL falcon tubes were filled with equal volume and were spun at 6000×g for 20 minutes to pellet bacterial cells and frozen until used. 28 conditions of pure and mixed solvents were used to extract protein. Briefly the pellet was weighed and extracted with 4 times (w/v) of the desired organic solvent. Samples were vortexed for 30 seconds and spun at 8000×g for 15 minutes. The supernatants were decanted into a new tube and evaporated under air. Samples were then resuspended and SDS-PAGE was run to determine protein purity. Gels were rinsed with water for 15 minutes 3 times and stained in colloidal Coomassie overnight.
Figure 25:
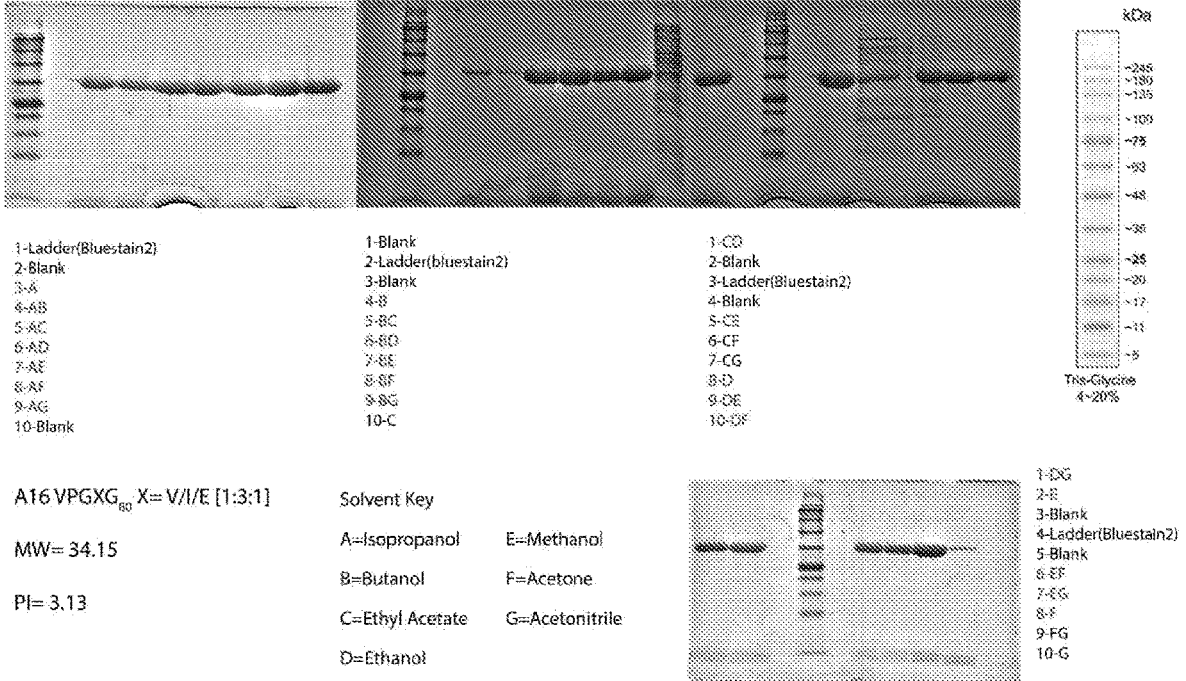
FIG. 25. Extraction Screen of Acidic A16 Elastin Like Polypeptide. Glycerol stocks were used to make an overnight starter culture of *E. coli*. 2 liter flasks containing 333 mL of terrific broth were inoculated and grown for 24 hours. 50 mL falcon tubes were filled with equal volume and were spun at 6000×g for 20 minutes to pellet bacterial cells and frozen until used. 28 conditions of pure and mixed solvents were used to extract protein. Briefly the pellet was weighed and extracted with 4 times (w/v) of the desired organic solvent. Samples were vortexed for 30 seconds and spun at 8000×g for 15 minutes. The supernatants were decanted into a new tube and evaporated under air. Samples were then resuspended and SDS-PAGE was run to determine protein purity. Gels were rinsed with water for 15 minutes 3 times and stained in colloidal Coomassie overnight.
Figure 26:
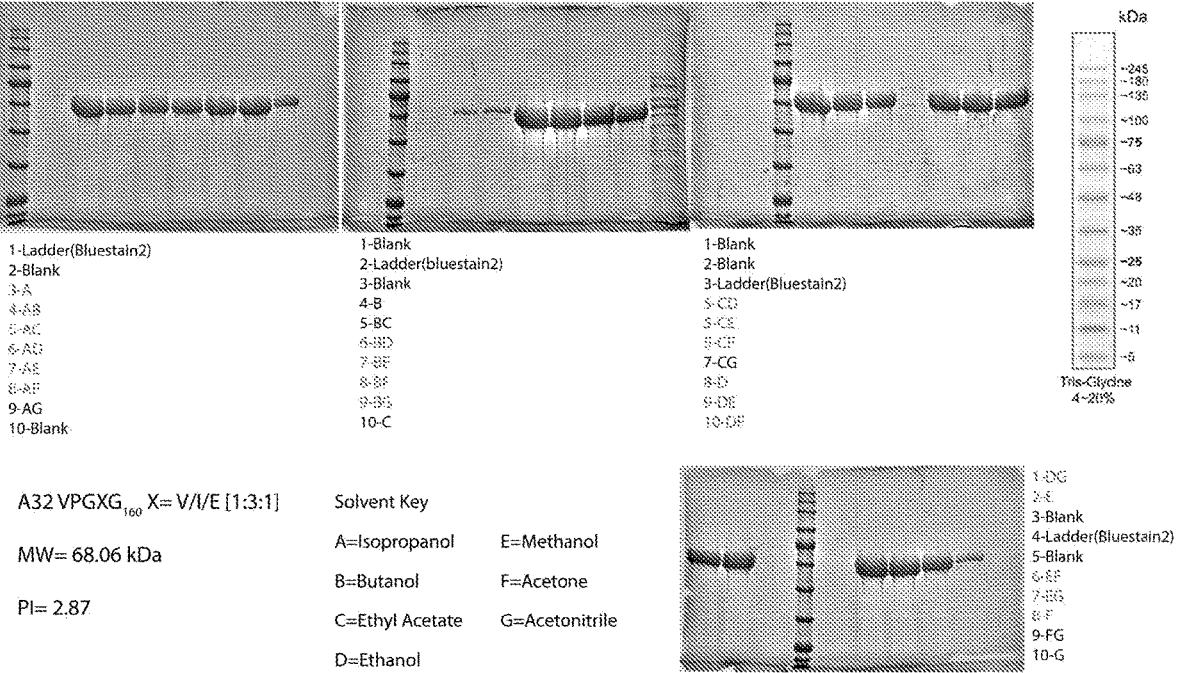
FIG. 26. Extraction Screen of Acidic A32 Elastin Like Polypeptide. Glycerol stocks were used to make an overnight starter culture of *E. coli*. 2 liter flasks containing 333 mL of terrific broth were inoculated and grown for 24 hours. 50 mL falcon tubes were filled with equal volume and were spun at 6000×g for 20 minutes to pellet bacterial cells and frozen until used. 28 conditions of pure and mixed solvents were used to extract protein. Briefly the pellet was weighed and extracted with 4 times (w/v) of the desired organic solvent. Samples were vortexed for 30 seconds and spun at 8000×g for 15 minutes. The supernatants were decanted into a new tube and evaporated under air. Samples were then resuspended and SDS-PAGE was run to determine protein purity. Gels were rinsed with water for 15 minutes 3 times and stained in colloidal Coomassie overnight.

We continued to evaluate the scope of contamination in ELP extracts by assaying for LPS content using the method reported by Zhu and colleagues that does not require any further separation operations. In brief, we ran SDS-PAGE gels as previously described and then rinsed them with H$_2$O for 1 min. As the data in FIG. 22 shows, there appears to be substantially less than 31 ng LPS content in a 50 µg sample of V12-K$_4$-V12 extract. Taken together, we infer from these findings that organic solvent extraction is capable of eliminating both LPS and nucleic acid contamination in ELP isolates.

Example 9. Additional ELP Extraction Data

Referring to FIGS. 23-34 and their Figure legends, different sized ELP protein extraction procedures and outcome were shown, using various solvents and conditions. Various solvent extractions are followed with hot spin and/or cold spin, dialysis combination to identify practical feasible polishing step.

Particularly, FIGS. 23-26 each demonstrate broad extractability to all the solvents tested in the experiments. Extraction is not limited to acidic or basic ELPs since N8 in FIG. 23 bears no formal charge. Extraction has shown success with smaller acidic ELP's such as A8 in FIG. 24. Extraction has shown success with moderate sized acidic ELP's such as A16 in FIG. 25. Extraction has shown success with large acidic ELP's such as A32 in FIG. 26.

Figure 27:
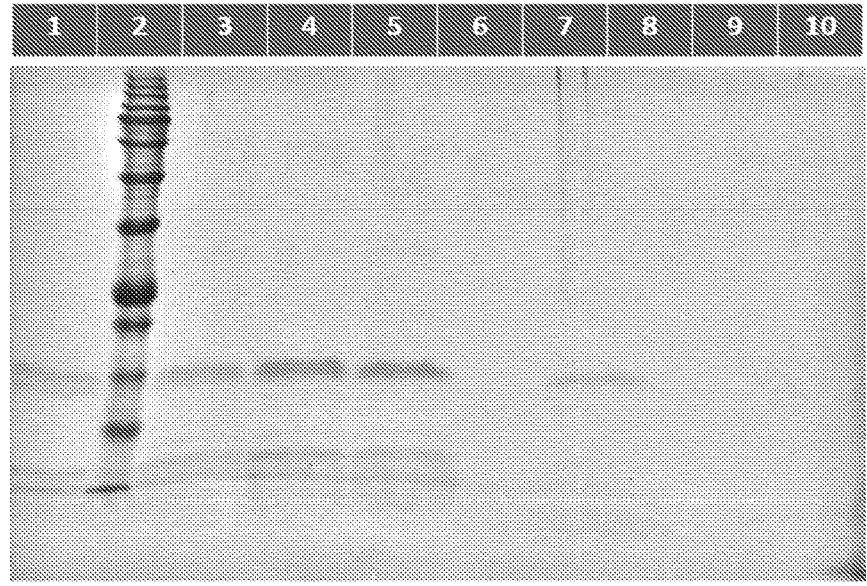
FIG. 27. Extraction Screen of Chimeric Epidermal Growth Factor-Elastin Like Polypeptide. Glycerol stocks were used to make an overnight starter culture of *E. coli*. 2 liter flasks containing 333 mL of terrific broth were inoculated and grown for 24 hours. 50 mL falcon tubes were filled with equal volume and were spun at 6000×g for 20 minutes to pellet bacterial cells and frozen until used. 6 conditions of pure and mixed solvents (v:v ratio) were used to extract protein. Briefly the pellet was weighed and extracted with 4 times (w/v) of the desired organic solvent. Samples were vortexed for 30 seconds and spun at 8000×g for 15 minutes. The supernatants were decanted into a new tube and evaporated under air. Samples were then resuspended and SDS-PAGE was run to determine protein purity. Gels were rinsed with water for 15 minutes 3 times and stained in colloidal Coomassie overnight.

FIG. 27 demonstrates extractability of fusion protein V24-EGF in varying solvents. Slight differences in yield and purity were observed by varying ratios and combinations of solvents.

Figure 28:
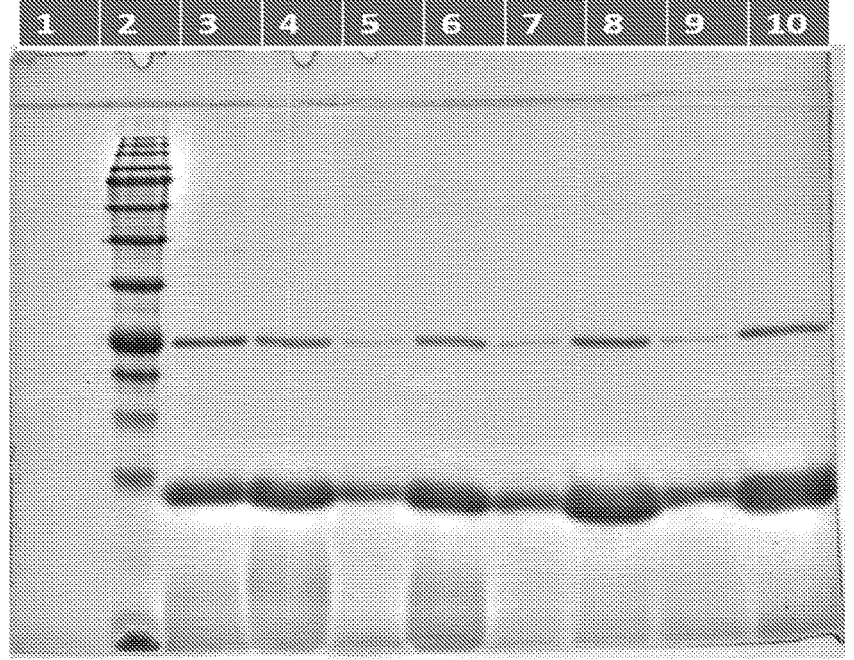
FIG. 28. Water vs. PBS for resuspension after cleaning spin. V12-K4-V12 was extracted with IPA:BuOH (1:1) mixture 4 times the *E. coli* pellet weight (w/v) by adding the organic solvent blend and vortexing for a minute. The slurry is spun down (6000×g, 15 mins) to remove the insoluble cell debris and the supernatant is collected by decanting into a new tube. Then, samples were precipitated by adding 100 percent acetone or acetonitrile till final volume is 70% v/v. The solution was centrifuged (6000×g, 10 mins) and supernatant was discarded, pellet was resuspended in water (well 3)/PBS (well 4) 1 times the weight (w/v) of the pellet. The solution was clarified by performing another round of centrifugation (6000×g, 10 mins) and supernatant was collected (wells 5 & 6). 20% v/v saturated solution of ammonium sulfate was added to supernatant after heating it up (37° C.) and the solution was spun down at 13000×g for 20 mins at 40° C. The supernatants were separated, and the pellets were resuspended in water (well 7)/PBS (well 8). The resuspended pellet underwent another hot spin water (well 9)/PBS (well 10). 5 μL sample+5 μL loading dye was loaded in each of the wells (15% SDS PAGE gel).

FIG. 28 compares water vs. PBS for resuspension after cleaning spin. It has shown that PBS solubilizes more of the polypeptide than water without adding more to the contaminant profile after cleaning spin (the last step of ACN precipitation).

Figure 29:
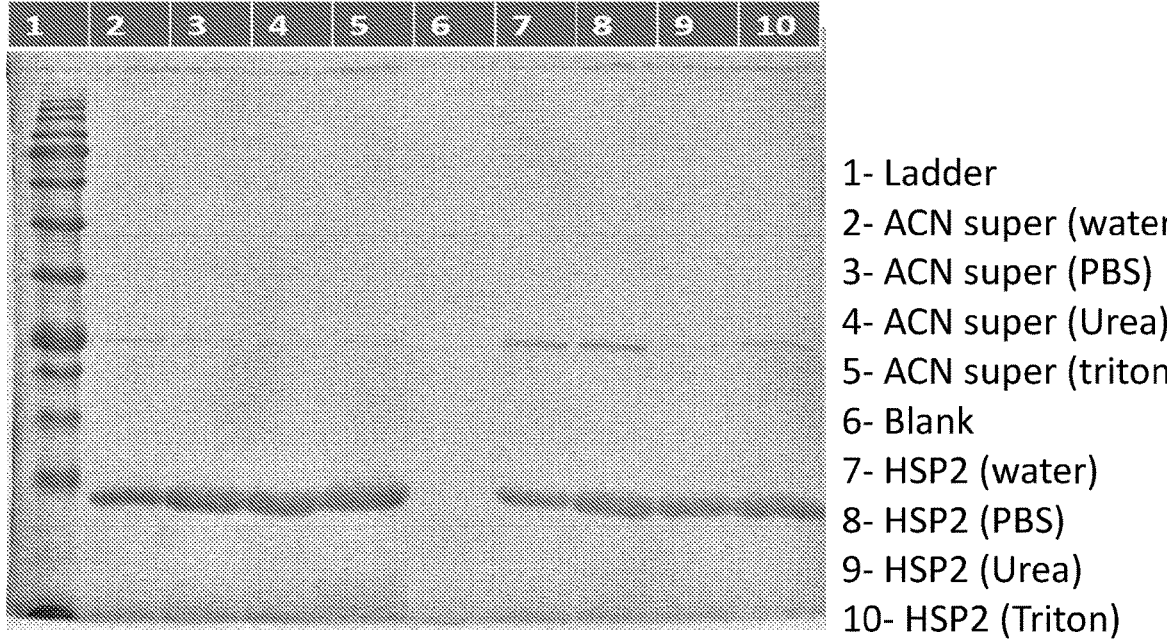
FIG. 29. Resuspension with different solvents. V12-K4-V12 was extracted with IPA:BuOH (1:1) mixture 4 times the weight of *E. coli* pellet (w/v) by adding the organic solvent blend and vortexing for a minute. The slurry is spun down (6000×g, 10 mins) to remove the insoluble cell debris and the supernatant is collected by decanting into a new tube. Then, samples were precipitated by adding 100 percent acetone or acetonitrile till final volume is 70% v/v. The solution was centrifuged (6000×g, 10 mins) and supernatant was discarded, pellet was resuspended in water (well2)/PBS (well3)/Urea (well4)/triton (well5) 1 times w/v of the pellet. 20% v/v saturated solution of ammonium sulfate was added to supernatant after heating it up (37° C.) and the solution was spun down at 13000×g for 15 mins at 40° C. The supernatants were separated, and the pellets were resuspended in water/PBS/urea/triton. The resuspended pellet was undergone another round of hot spin and the pellets were resuspended in water (well7)/PBS (well8)/urea (well9)/triton (well10). 5 μL sample+5 μL loading dye was loaded in each of the wells (15% SDS PAGE gel).

FIG. 29 compares resuspension with different solvents. There was not any significant difference based on visionary analysis of band intensity among solvents other than water. To avoid adding complexity, PBS had been chosen as the solvent of interest.

Figure 30:
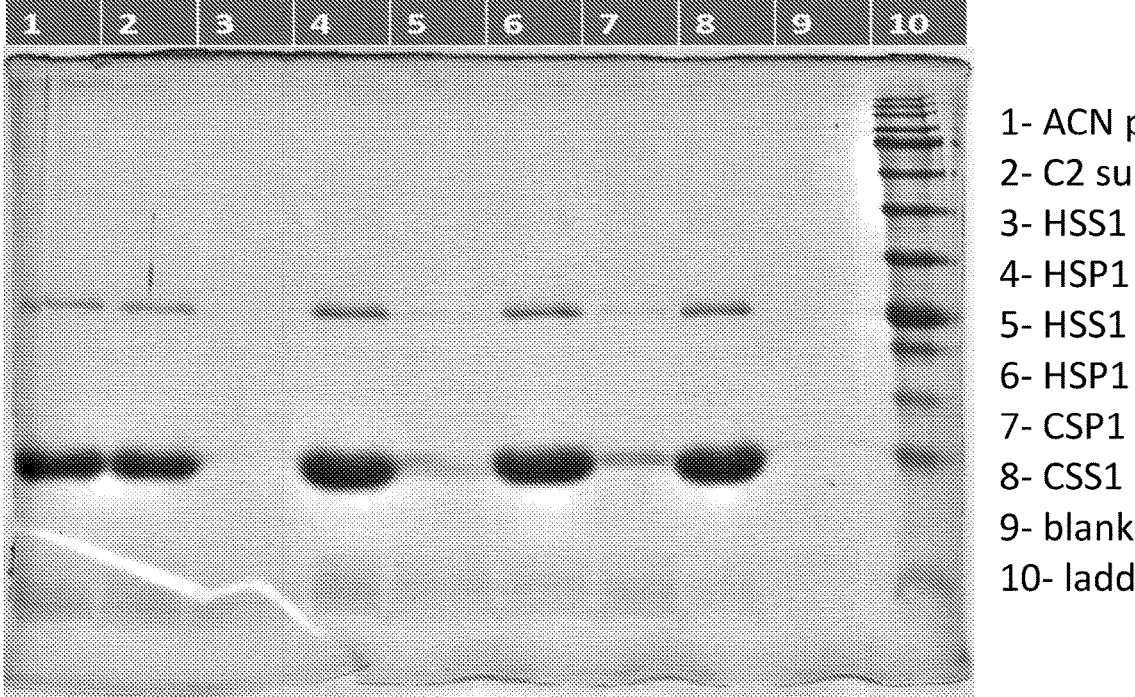
FIG. 30. ITC-HS vs HS-CS-loading-V12-K4-V12-required ITC. V12-K4-V12 was extracted with IPA:BuOH (1:1) mixture 4 times the weight of *E. coli* pellet (w/v) by adding the organic solvent blend and vortexing for a minute. The slurry is spun down (6000×g, 15 mins) to remove the insoluble cell debris and the supernatant is collected by decanting into a new tube. Then, samples were precipitated by adding 100 percent acetone or acetonitrile till final volume is 70% v/v. The solution was centrifuged (6000×g, 10 mins) and supernatant was discarded, pellet was resuspended in PBS (well1) 1 time the weight of pellet (w/v). The solution was cleaned up by doing another round of centrifugation (6000×g, 10 mins) and supernatant was collected (well 2). 20% v/v saturated solution of ammonium chloride was added to supernatant after heating it up (37° C.) and the solution was spun down at 13000×g for 20 mins at 40° C. The supernatants were separated and the pellets were resuspended in PBS (done in duplicate on bacterial pellets derived from the same culture (HSS—wells3,5; HSP1—wells 4,6). The resuspended pellet was kept in ice for 15 mins and underwent a cold spin at 10000×g, 15 mins at 4° C. The supernatant (well 8) was separated from the pellet (well7). 5 μL sample+5 μL loading dye was loaded in each of the wells (15% SDS PAGE gel).

FIG. 30 demonstrates procedure of ITC-HS vs HS-CS-loading-V12-K4-V12-required ITC.

There doesn't seem to be a significant difference between purification procedure involving just hot spin vs. the one with hot spin followed by cold spin. So, for further processes, either dialysis or just one round of hot spin is used as the final polishing step.

Figure 31:
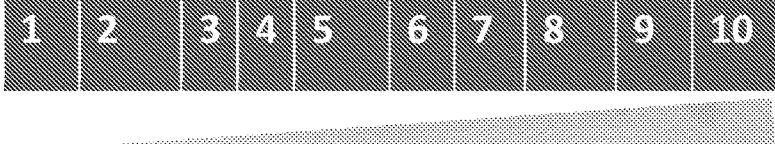
FIG. 31. ACN vs Acetone-cold vs RT-A32-68 kDa-5 μL loading. A32 was extracted with IPA:BuOH (1:1) mixture 4 times the weight of *E. coli* pellet (w/v) by adding the organic solvent blend and vortexing for a minute. The slurry is spun down (8000×g, 15 mins) to remove the insoluble cell debris and the supernatant is collected by decanting into a new tube. Then, samples were precipitated by adding 100 percent acetone or acetonitrile till final volume is 70% v/v. The solution was centrifuged (8000×g, 15 mins) and supernatant was discarded, pellet was resuspended in PBS (wells1,2,5 &6) 1 time the weight of pellet (w/v). The solution was cleaned up by doing another round of centrifugation (8000×g, 15 mins) and supernatant was collected (wells 7 & 8). 5 μL sample+5 μL loading dye was loaded in each of the wells (15% SDS PAGE gel). Wells 3,4,8 shows that precipitation didn't work if back extraction with ethyl acetate-2 times v/v of IPA:BuOH mixture was performed first.
Figure 31:
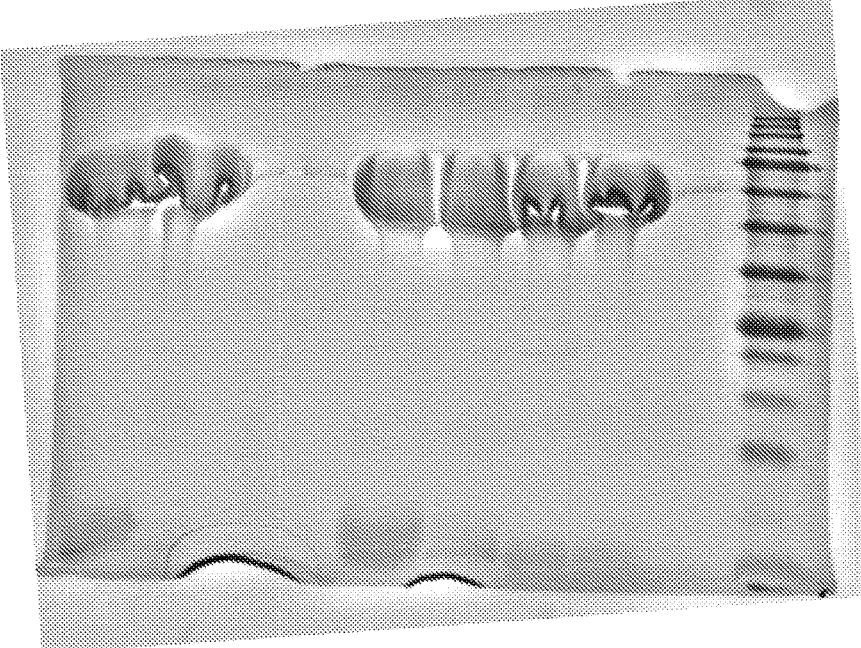

FIG. 31 compares ACN vs Acetone-cold vs RT-A32-68 kDa-5 µL loading. Room temperature precipitation worked almost like cold and ACN works like acetone. To avoid an extra complexity, further processes were carried at room temperature. The precipitation doesn't work after performing back extraction.

Figure 32:
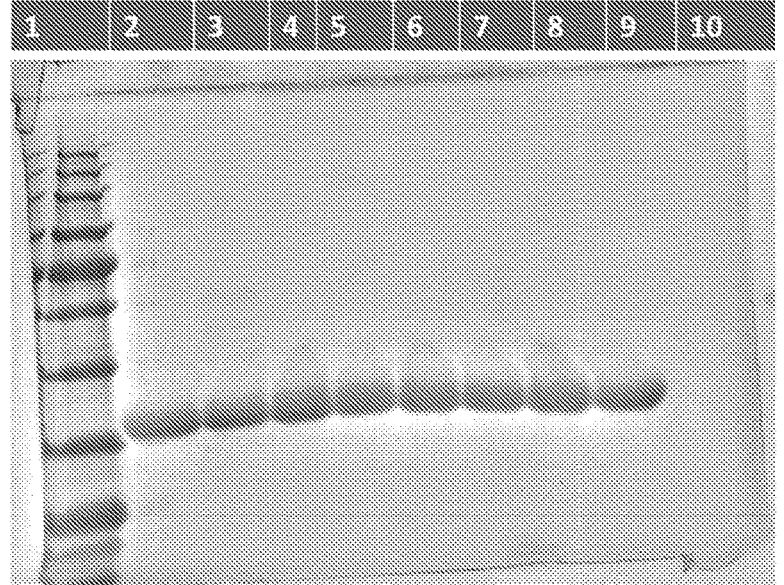
FIG. 32. ACN vs Acetone-cold vs RT-A16-loading. A16 was extracted with IPA:BuOH (1:1) mixture 4 times the weight of *E. coli* pellet (w/v) by adding the organic solvent blend and vortexing for a minute. The slurry is spun down (8000×g, 15 mins) to remove the insoluble cell debris and the supernatant is collected by decanting into a new tube. Then, samples were precipitated by adding 100 percent acetone or acetonitrile till final volume is 70% v/v. The solution was centrifuged (8000×g, 15 mins) and supernatant was discarded, pellet was resuspended in PBS 1 time w/v of the pellet. The solution was cleaned up by doing another round of centrifugation (8000×g, 15 mins) and supernatant was collected (wells2,4,6 & 8). 20% v/v saturated solution of ammonium chloride was added to supernatant after heating it up (37° C.) and the solution was spun down at 13000×g for 20 mins at 40° C. The supernatants were separated and the pellets were resuspended in water (wells 3,5,7 & 9). 5 μL sample+5 μL loading dye was loaded in each of the wells (10% SDS PAGE gel).

FIG. 32 compares ACN vs Acetone-cold vs RT-A16-loading. Again, it is shown similar results for both ACN and acetone, cold and room temperature were similar as well. No polypeptide length dependent trends came out in the given size range.

Figure 33:
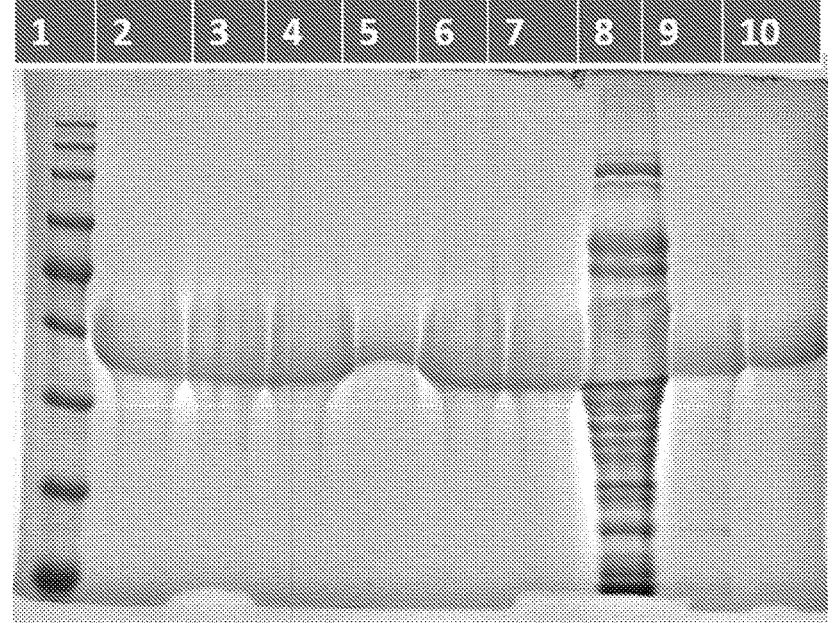
FIG. 33. A32 various purification. Polar Organic Extraction: An *E. coli* cell pellet was extracted with 4 times the bacterial pellet weight (w/v) with a IPA:BuOH (1:1) mixture by adding the organic solvent blend and vortexing for a minute unless otherwise stated. The slurry is spun down (10000×g, 15 mins) to remove the insoluble cell debris and the supernatant is collected by decanting into a new tube. A sample was taken and evaporated and resuspended in PBS 1 time w/v of the pellet. (well2). Another sample underwent a round of hot spin and was loaded in well3.

FIG. 33 demonstrates various purification schemes for A32. Extraction alone showed high yield of ELP and can be accomplished within approximately 15 minutes. Addition of acetonitrile precipitation shows minimal loss of protein while removing excess organic solvent better than back extraction. Cell lysis followed by ITC compared to extraction and precipitation takes longer and shows a greater loss in yield. (It is noted that no strong conclusions should be based on lane five due to possible experimental error, while evaporating sample loss occurred thus final yield does not depict usual yield achieved).

FIG. 34 demonstrates A8 various purification. Extraction showed high level of purity in approximately 15 minutes. Further purification using either back extraction or hot spins showed small loss in protein. Cell lysate followed by multiple hot spins showed loss in protein (see lane 3) and difficulty in removing all protein contamination.

Example 10. Toward Understanding the ELP Extraction Mechanism

We initially expected amphiphilic ELP to be amenable to organic extraction because of their relative hydrophobicity and hydrophilicity as reported for GFP; however, the ELP extraction mechanism appears to be more complex. Based on an analysis of our initial screens of three similar ELP variants, we have not been able to discern any clear trends between the various rankings of solvent polarity and relative ELP hydrophobicity (Table 4 and Table 1 respectively). Additionally, no obvious connection existed between other solvent properties, such as hydrogen bonding potential.

When considering ELP extractability for all the organic solvents used in the screens, nBuOH clearly stands out among the other alcohols. We originally chose nBuOH because it precipitated non-target *E. coli* proteins during TEL extraction. It had also been reported in the GFP extraction literature as a means to efficiently push the ethanol-solubilized GFP into an aqueous phase, whereas tBuOH promoted GFP precipitation. Based on this background information, we expected that moderate amounts of nBuOH would not solubilize ELP and might serve as a useful back-extractant.

For the three triblock ELP assessed, pure nBuOH was unable to extract any target ELP, whereas pure IPA achieved successful extraction in two of the three cases. The lower alcohols, EtOH and MeOH, were able to extract all three ELP; however, they also tended to co-extract a number of other proteins. When used in combination with other solvents, nBuOH had the lowest promiscuity toward co-extraction of contaminating proteins, while IPA blends showed comparable results.

Figure 9:
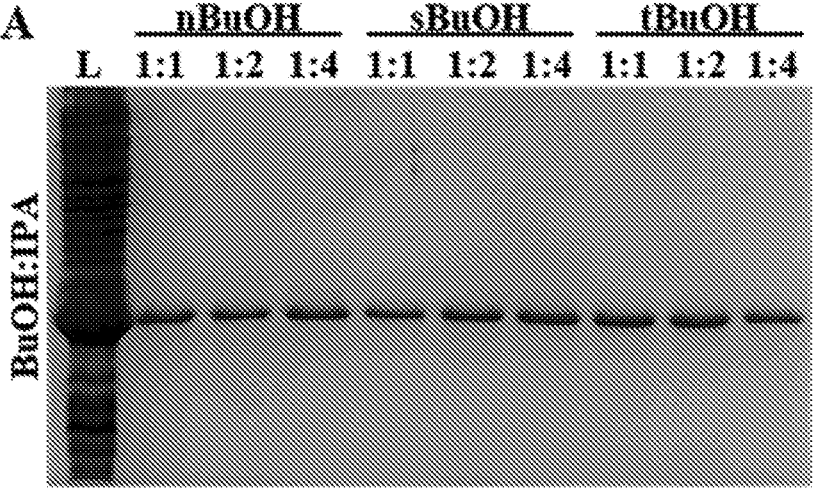
FIG. 9. SDS-PAGE analysis of butanol isomer extraction efficiency in solvent blends with (A) IPA, (B) EtOH, and (C) MeOH for recovering ELP V24-$K_4$-V24 from cell lysates. Blend ratios (v/v) are as indicated for each solvent combination. L=lysate.
Figure 9:
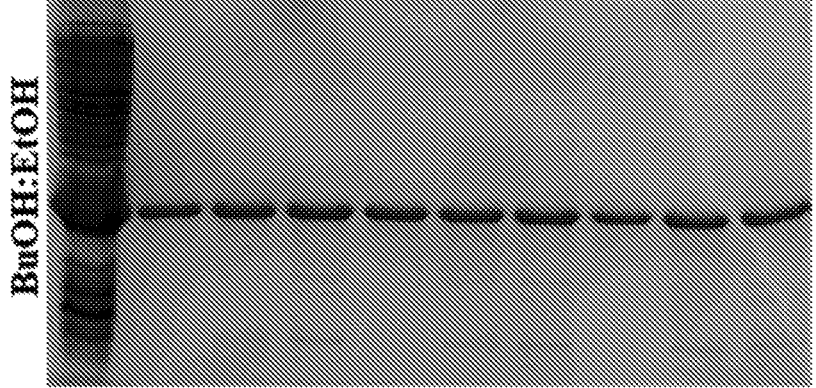
Figure 9:
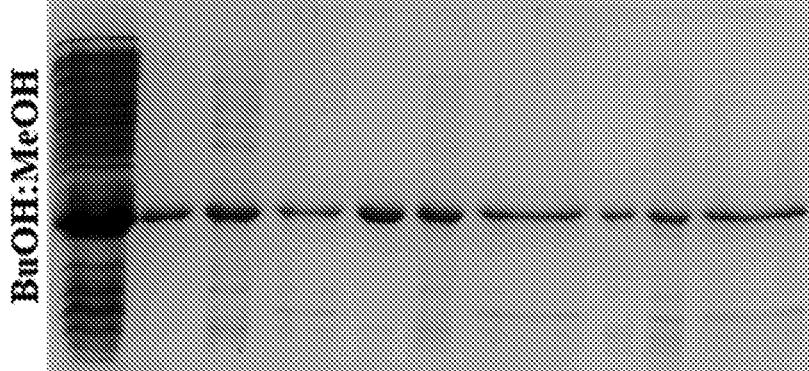

Even though nBuOH was poor at extracting ELP on its own, we were surprised by the high ELP selectivity it provided when used in combination with other solvents. To gain further insight into this high extraction performance, we investigated the effect of butanol isomerism on ELP extractability. Working with V24-K$_4$-V24 lysates, we compared nBuOH, sBuOH, and tBuOH in combination with the other alcohols (FIG. 9).

Unexpectedly, extraction efficiency and selectivity appear to be unaffected by the butanol isomer employed. When combined with IPA or EtOH, 50% butanol in the organic extractant phase is sufficient to eliminate extraction of non-target proteins without a noticeable change in yield, regardless of the butanol isomer used. Extraction yield and selectivity are similar for 1:1 butanol:MeOH mixtures, whereas these qualities deteriorated at 1:2 and 1:4 butanol:MeOH ratios. The combination of butanol with IPA was the most effective in providing both high yield and purity with a minimal amount of butanol. Butanol:EtOH mixtures were also quite effective; however, an increasing amount of low molecular weight protein contamination occurred with decreasing butanol content.

These data with simple alcohol extractants demonstrate the influence of all butanol isomers in equally increasing extractant selectivity without sacrificing yield. Further, for V24-K$_4$-V24 extraction, these data further show that increasing alcohol molecular weight and/or decreasing polarity plays a role in the extraction mechanism and increases selectivity for ELP over non-ELP proteins. This trend is expected to be dependent on the ELP of interest. Additional studies with a broader set of ELP and higher molecular weight alcohols may provide additional insights into the extraction mechanism.

Figure 11:
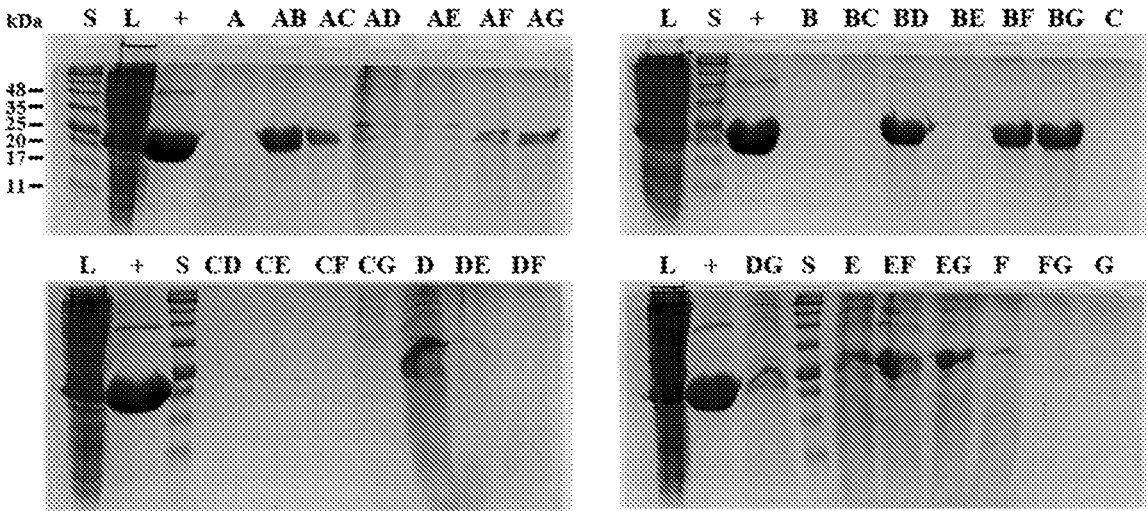
FIG. 11. SDS-PAGE analysis of V24-K$_4$-V24 extraction screen. S=protein MW standards, L=clarified lysate, "+"=3× ITC-purified V24-K$_4$-V24. Extractants used are listed in Table.

In addition to the ability of butanol to increase extraction selectivity, this solvent also enhanced extraction yields when blended with other solvents. For example, neither nBuOH nor ACN was able to extract to any appreciable extent the three lysine-containing ELP from lysates. The combination of nBuOH and ACN; however, showed a moderate-to-large amount of extracted ELP for each variant. Although most obvious for nBuOH:ACN, we also observed this effect when using nBuOH:IPA, IPA:EtOAc, and IPA:ACN for V24-K$_4$-V24 extraction (FIG. 11). The peculiar behavior of butanol toward ELP extractability enhancement remains unclear from the current data, although we expect that the ELP may exist in the organic phase as a micro- or nanoemulsion mediated by solvent-solvent interactions and residual water from the lysate or cells. Studies investigating the underlying basis for the success of these mixed solvent extractants will be needed to guide the rational selection of organic solvents for extracting a particular ELP construct.

Abbreviations elastin-like polypeptides (ELP), lower critical solution temperature (LCST), inverse transition cycling (ITC), green fluorescent protein (GFP), tropoelastin (TEL), alcohol dehydrogenase (ADH), lipopolysaccharide (LPS), methanol (MeOH), ethanol (EtOH), 2-propanol (IPA), 1-butanol (nBuOH), 2-butanol (sBuOH), 2-methyl-2-propanol (tBuOH), acetone (Ace), acetonitrile (ACN), ethyl acetate (EtOAc), acetic acid (HOAc). #HS: number of hot spins, HSP #: Hot spin pellet (#—number of rounds of ITC), HSS #: Hot spin supernatant (#—number of rounds of ITC), CSP #: Cold spin pellet (#—number of rounds of ITC), CSS #: Cold spin supernatant (#—number of rounds of ITC), BE: back extraction, BuOH: Butanol, RT: Room temperature.

TABLE 4

| | | Organic Solvents and Properties. | | | | | | | | |
|---|---|---|---|---|---|---|---|---|---|---|
| Solvent | Notation | Formula | MW | Density | Solubility | Dielectric | Relative | Polarity | Polarity | Log P$^g$ |
| Acetone | Ace | (CH$_3$)$_2$CO | 58.09 | 0.784 | Miscible | 21.0 | 0.355 | 42.2 | 5.1 | −0.24 |
| Acetonitrile | ACN | CH$_3$CN | 41.06 | 0.782 | Miscible | 36.6 | 0.460 | 45.6 | 5.8 | −0.34 |
| n-Butanol | nBuOH | C$_4$H$_9$OH | 74.14 | 0.806 | 6.32 | 17.8 | 0.586 | 49.7 | 3.9 | 0.88 |
| sec-Butanol | sBuOH | CH$_3$CHOHCH$_2$C | 74.14 | 0.802 | 18.1 | 17.3 | 0.506 | 47.1 | — | 0.61 |
| tert-Butanol | tBuOH | (CH$_3$)$_3$COH | 74.14 | 0.8 | Miscible | 12.5 | 0.389 (30) | 43.3 | 3.9 | 0.35 |
| Diethyl ether | Et$_2$O | (C$_2$H$_5$)$_2$O | 74.14 | 0.708 | 6 | 4.27 | 0.117 | 34.5 | 2.8 | 0.89 |
| Ethanol | EtOH | C$_2$H$_5$OH | 46.07 | 0.794 | Miscible | 25.3 | 0.654 | 51.9 | 5.2 | −0.31 |
| Ethyl acetate | EtOAc | C$_4$H$_8$O$_2$ | 88.12 | 0.895 | 8 | 6.08 | 0.228 | 38.1 | 4.4 | 0.73 |

TABLE 4-continued

| | | | | | | | | | | |
|---|---|---|---|---|---|---|---|---|---|---|
| Solvent | Notation | Formula | MW | Density | Solubility | Dielectric | Relative | Polarity | Polarity | Log P$^g$ |
| MeOH | MeOH | $CH_3OH$ | 32.05 | 0.786 | Miscible | 33.0 | 0.762 | 55.4 | 5.1 | −0.77 |
| Isopropanol | IPA | $CH_3CHOHCH_3$ | 60.11 | 0.786 | Miscible | 20.2 | 0.546 | 48.4 | 3.9 | 0.05 |
| Water | $H_2O$ | $H_2O$ | 18.01 | 1 | — | 80.1 | 1.00 | 63.1 | 10.2 | −1.38 |

Organic Solvents and Properties.

[a] Density (specific gravity). [3 3 3 3 3]
[b] Solvent solubility in water. [3 3 3 3 3]
[c] Dielectric constant (relative permittivity, $\varepsilon$). [4 4 4 4 4]
[d] Relative solvent polarity ($E_T^N$) measured at 25° C., except for tBuOH at 30° C.. [5 5 5 5 5]
[e] Polarity parameter ($E_T$). [3 3 3 3 3]

---

The invention claimed is:

1. A method to purify Elastin like polypeptides (ELPs) from a total cell lysate, comprising:
   a. Preparing a clarified cell lysate, wherein said cell lysate comprises at least one ELP with or without fusing to other proteins;
   b. Preparing at least one organic extractant using an organic solvent, wherein the organic solvent is selected from the group consisting of IPA, nBuOH, EtOAc, Ace, ACN, EtOH and MeOH, or a combination thereof;
   c. Adding said cell lysate to the organic extractant to form a mixture;
   d. Vortexing the mixture and subjecting the mixture to centrifugation to separate out an organic phase; and
   e. Selectively recovering the organic phase, which comprises said at least one ELP with or without fusing to other proteins.

2. The method according to claim 1, further comprising adding an aqueous salt solution to the recovered organic phase of extractant, and repeating steps d and e.

3. A method to purify Elastin like polypeptides (ELPs) from whole cells that express at least one ELP with or without fusing to other proteins, comprising:
   a. Preparing whole cell pellets comprising at least one ELP with or without fusing to other proteins;
   b. Mixing an organic solvent with said whole cell pellets to form a first mixture, wherein the organic solvent is selected from the group consisting of IPA, nBuOH, EtOAc, Ace, ACN, EtOH and MeOH, or a combination thereof;
   c. Vortexing the first mixture and subjecting the first mixture to centrifugation until a first organic phase is formed;
   d. Selectively collecting the first organic phase;
   e. Adding anti-solvent and water to the first organic phase to form a second mixture;
   f. Subjecting the second mixture to centrifugation until an aqueous phase and a second organic phase are formed; and
   g. Removing the second organic phase to recover the purified (back-extracted) ELP in the aqueous phase.

4. A method to purify Elastin like polypeptides (ELPs) from whole cells that express at least one ELP with or without fusing to other proteins, comprising:
   a. Preparing whole cell pellets comprising at least one ELP with or without fusing to other proteins;
   b. Mixing an organic solvent with said whole cell pellets to form a first mixture, wherein the organic solvent is selected from the group consisting of IPA, nBuOH, EtOAc, Ace, ACN, EtOH and MeOH, or a combination thereof;
   c. Vortexing the first mixture and subjecting the first mixture to centrifugation until a first organic phase is formed;
   d. Selectively collecting the first organic phase;
   e. Adding acetonitrile to the collected organic phase to form a second mixture;
   f. Subjecting the second mixture to centrifugation until a pellet and a second organic phase are formed;
   g. Removing the second organic phase to recover the pelleted (precipitated) ELP and placing it back in an aqueous phase solution; and
   h. Subjecting the aqueous phase solution to centrifugation to remove contaminants and recovering ELP in an aqueous phase by collecting a supernatant.

5. The method according to claim 1, wherein the ELP is selected from the group consisting of SEQ ID Nos: 3-13 (V12, V24, S12-K4-S12, V12-K4-V12, V24-K4-V24, CryS96, V24-EGF, N8, A8, A16, and A32, respectively).

6. The method according to claim 1, wherein the ratio of organic solvents in combination is about 1:1.

7. The method according to claim 1, wherein the recovered ELP is substantially nucleic acid free.

8. The method according to claim 1, wherein the recovered ELP is substantially lipopolysaccharide (LPS) free.

9. The method according to claim 1, wherein the purification time of ELP is reduced compared to the conventional inverse transition cycling (ITC) method.

10. The method according to claim 1, wherein the ratio of organic solvents in combination is selected from 1:1, 1:2, 1:4, 2:1 and 4:1.

*    *    *    *    *